US009603798B2

(12) United States Patent
Chiang et al.

(10) Patent No.: US 9,603,798 B2
(45) Date of Patent: Mar. 28, 2017

(54) ANTIBODY-CONJUGATED DOUBLE-EMULSION NANOCAPSULE AND PREPARATION METHODS THEREOF

(71) Applicant: National Chiao Tung University, Hsinchu (TW)

(72) Inventors: Chih-Sheng Chiang, Taichung (TW); Shang-Hsiu Hu, Taipei (TW); San-Yuan Chen, Hsinchu (TW)

(73) Assignee: NATIONAL CHIAO TUNG UNIVERSITY, Hsinchu (TW)

( * ) Notice: Subject to any disclaimer, the term of this patent is extended or adjusted under 35 U.S.C. 154(b) by 142 days.

(21) Appl. No.: 14/260,726

(22) Filed: Apr. 24, 2014

(65) Prior Publication Data

US 2014/0356421 A1   Dec. 4, 2014

(30) Foreign Application Priority Data

May 31, 2013   (TW) .............................. 102119370 A
Nov. 5, 2013   (TW) .............................. 102140127 A

(51) Int. Cl.

| A61K 9/48 | (2006.01) |
|---|---|
| A61K 9/113 | (2006.01) |
| A61K 33/26 | (2006.01) |
| A61K 33/32 | (2006.01) |
| A61K 39/395 | (2006.01) |
| A61K 47/32 | (2006.01) |
| A61K 31/704 | (2006.01) |
| A61K 9/00 | (2006.01) |
| A61K 9/51 | (2006.01) |
| C07K 16/32 | (2006.01) |
| A61K 47/48 | (2006.01) |
| A61K 31/337 | (2006.01) |
| A61K 31/4745 | (2006.01) |
| A61K 45/06 | (2006.01) |
| A61K 39/00 | (2006.01) |

(52) U.S. Cl.
CPC ............ *A61K 9/113* (2013.01); *A61K 9/0009* (2013.01); *A61K 9/5138* (2013.01); *A61K 31/337* (2013.01); *A61K 31/4745* (2013.01); *A61K 31/704* (2013.01); *A61K 39/3955* (2013.01); *A61K 45/06* (2013.01); *A61K 47/32* (2013.01); *A61K 47/48569* (2013.01); *A61K 47/48869* (2013.01); *C07K 16/32* (2013.01); *A61K 2039/505* (2013.01)

(58) Field of Classification Search
None
See application file for complete search history.

(56) References Cited

U.S. PATENT DOCUMENTS

| 4,496,689 | A * | 1/1985 | Mitra ................. A61K 47/4823 435/174 |
|---|---|---|---|
| 6,872,696 | B2 | 3/2005 | Becker et al. |
| 2005/0058603 | A1 | 3/2005 | Gao et al. |
| 2005/0130167 | A1 | 6/2005 | Bao et al. |
| 2007/0116951 | A1 | 5/2007 | Kwon et al. |
| 2007/0258889 | A1 | 11/2007 | Douglas et al. |
| 2008/0286350 | A1 | 11/2008 | Bally et al. |
| 2009/0196827 | A1 | 8/2009 | Wheatley et al. |
| 2009/0324494 | A1 | 12/2009 | Ham et al. |
| 2010/0092384 | A1 | 4/2010 | Bumb et al. |
| 2011/0159291 | A1 | 6/2011 | Sun et al. |
| 2012/0107270 | A1 | 5/2012 | Kaspar et al. |
| 2012/0108563 | A1 | 5/2012 | Grayzel |
| 2012/0308560 | A1 | 12/2012 | Moore et al. |
| 2013/0137917 | A1 | 5/2013 | Liao et al. |

FOREIGN PATENT DOCUMENTS

| CN | 1632889 A | 6/2005 |
|---|---|---|
| CN | 101318710 A | 12/2008 |
| CN | 201207042 Y | 3/2009 |
| CN | 101475222 A | 7/2009 |
| CN | 101536982 A | 9/2009 |
| CN | 102128864 A | 7/2011 |
| CN | 102580106 A | 7/2012 |
| CN | 102746474 A | 10/2012 |
| JP | 2000203810 A | 7/2000 |
| WO | 9962079 A1 | 12/1999 |
| WO | 2004/069169 | 8/2004 |
| WO | WO2004/069169 * | 8/2004 |
| WO | 2006037229 A1 | 4/2006 |
| WO | 2007002690 A2 | 1/2007 |
| WO | 2009/037310 | 3/2009 |
| WO | 2009154651 A1 | 12/2009 |
| WO | 2010134087 A1 | 11/2010 |
| WO | 2011069074 A2 | 6/2011 |
| WO | 2012078771 A1 | 6/2012 |

OTHER PUBLICATIONS

Chiang et al (Nanomedicine: Nanotechnology, Biology and Medicine, Jan. 2014, vol. 10, pp. 99-107).*
Hu et al (ACS Nano, 2012, vol. 6, pp. 2558-2565).*
Baselga et al (Cancer Research 1998, vol. 58, pp. 2825-2831).*
Chiang et al, supplement to (Nanomedicine: Nanotechnology, Biology and Medicine, Jan. 2014, vol. 10, pp. 99-107).*
Lee et al (Molecules and Cells, Apr. 30, 2013, vol. 35, pp. 274-284).*
Kakinoki et al (Biol Pharm Bull, 2008, vol. 31, pp. 963-969).*
Lee (Nature Medicine, 2007, vol. 13, pp. 95-99).*
Arano et al (Bioconjugate Chemistry, 1991, vol. 2, pp. 71-76).*
Lee Alz et al., "The co-delivery of paclitaxel and Herceptin using cationic micellar nanoparticles." Biomaterials 30 (2009), p. 919-927.

(Continued)

*Primary Examiner* — Karen Canella
(74) *Attorney, Agent, or Firm* — McClure, Qualey & Rodack, LLP

(57) ABSTRACT

An antibody-conjugated double-emulsion nanocapsule is provided. A linking group is introduced on the surface of a double-emulsion nanocapsule, which is composed of an oily shell enclosing an aqueous core, to link the double-emulsion nanocapsule with an antibody.

24 Claims, 15 Drawing Sheets

(56) References Cited

OTHER PUBLICATIONS

Wang H et al., "Enhanced anti-tumor efficacy by co-delivery of doxorubicin and paclitaxel with amphiphilic methoxy PEG-PLGA copolymer nanoparticles." Biomaterials 32 (2011), p. 8281-8290.
Lee JH et al., "Combination Drug Delivery Approaches in Metastatic Breast Cancer." Journal of Drug Delivery, vol. 2012.
Chiang CH et al., "Enhancement of cancer therapy efficacy by trastuzumab-conjugated and pH-sensitive nanocapsules with the simultaneous encapsulation of hydrophilic and hydrophobic compounds." Nanomedicine, Jul. 13, 2013.

* cited by examiner

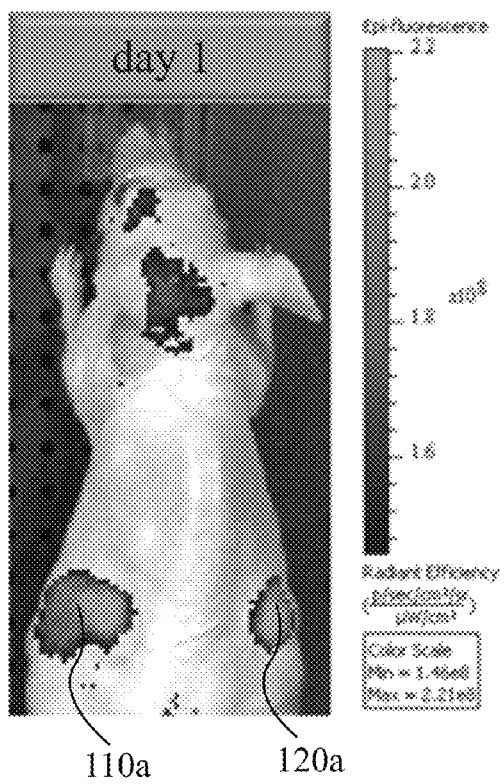 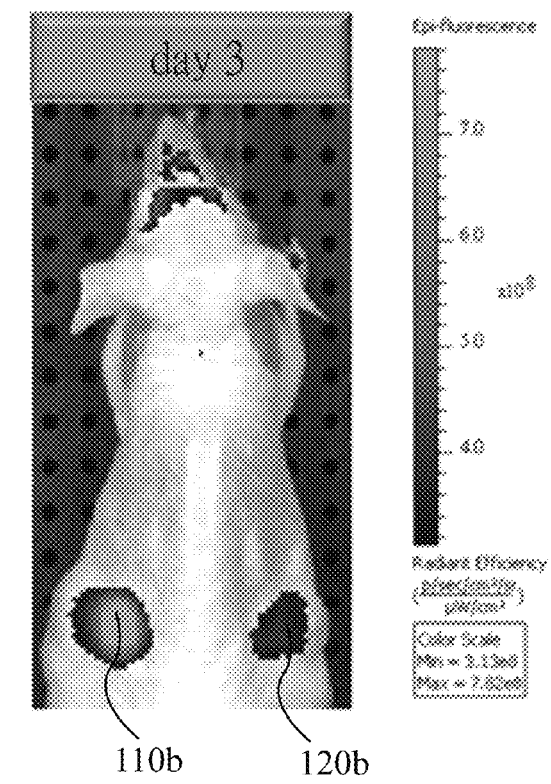
Fig. 10A       Fig. 10B
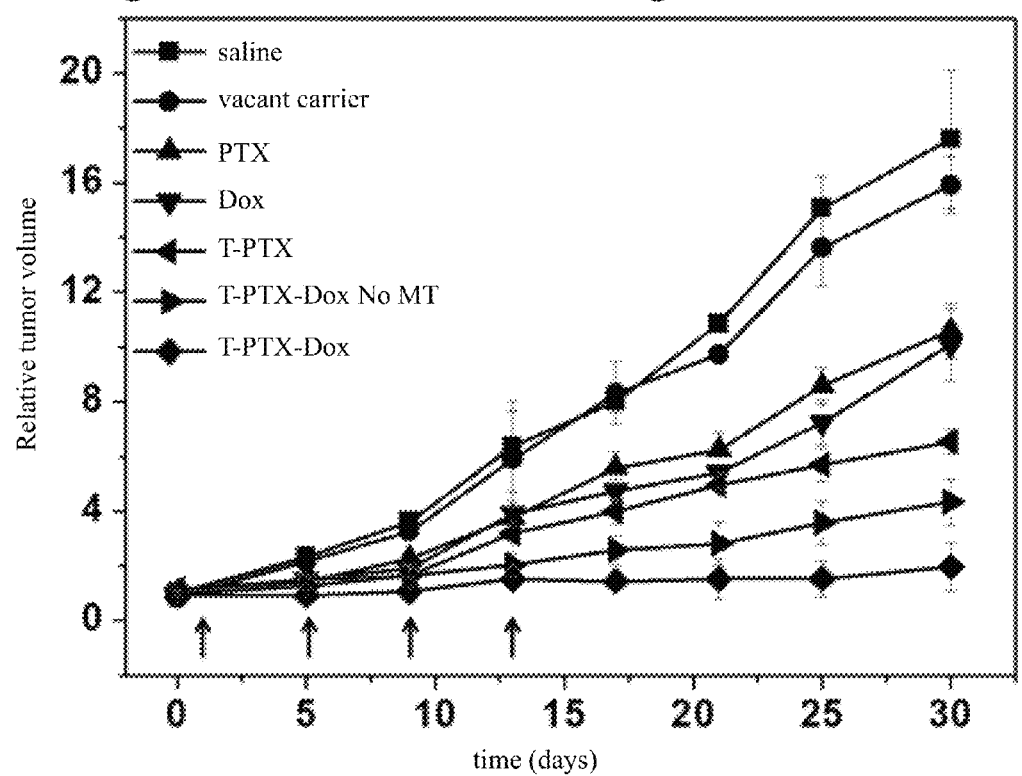
Fig. 11

ANTIBODY-CONJUGATED DOUBLE-EMULSION NANOCAPSULE AND PREPARATION METHODS THEREOF

CROSS-REFERENCE TO RELATED APPLICATION

This application claims the priority benefit of Taiwanese application serial no. 102119370, filed May 31, 2013 and Taiwanese application serial no. 102140127, filed Nov. 5, 2013, the full disclosure of which are incorporated herein by references.

BACKGROUND

Technical Field

The disclosure relates to an antibody-conjugated nanostructure. More particularly, the disclosure relates to an antibody-conjugated double-emulsion nanocapsule.

Description of Related Art

At present, some nanocapsules, having nanocapsules, are prepared from organic material to be a drug carrier for carrying drug. These nanocapsules include liposomes composed of lipid bilayer and micelles composed of amphoteric polymer. However, the structure of these nanocapsules is unstable, and the preparation of these nanocapsules is complex and thus is difficult to be controlled.

SUMMARY

In one aspect, an antibody-conjugated double-emulsion nanocapsule is provided. The antibody-conjugated double-emulsion nanocapsule, having a diameter of about 50 nm to about 400 nm, comprises an aqueous core, an oily shell enclosing the aqueous core, and at least an antibody. A composition of the oily shell comprises a polymer and a plurality of hydrophobic magnetic nanoparticles but does not comprise other surfactants. The polymer is a linking polyvinyl alcohol or a combination of polyvinyl alcohol (PVA) and a linking polymer, and the linking polyvinyl alcohol and the linking polymer above have a linking group. The antibody is chemically bonded to the linking group via a coupling agent.

According to some embodiments, the linking group may be a carboxylic group, a thiol group, an aldehyde group, an amine group, or a hydroxyl group.

According to some other embodiments, the linking polyvinyl alcohol is carboxymethylated polyvinyl alcohol (CMPVA), thiolated polyvinyl alcohol (TPVA), or a copolymer of PVA-TPMAA.

According to some other embodiments, the linking polymer is polyacrylic acid (PAA), polymethacrylic acid (PMAA), carboxymethylated polyvinyl alcohol (CMPVA), thiolated polyvinyl alcohol (TPVA), thiolated polymethacrylic acid (TPMAA), or a copolymer of PVA-TPMAA.

According to some other embodiments, the hydrophobic magnetic nanoparticles are nanoparticles having a hydrophobic functional groups-modified surface and made from $Fe_2O_3$, $Fe_3O_4$, $CoFe_2O_4$, or $MnFe_2O_4$.

According to some other embodiments, the antibody comprises breast cancer antibody of trastuzumab, colorectal cancer antibody of cetuximab, epidermal growth factor receptor antibody of panitumumab, or angiogenesis inhibitor antibody of bevacizumab.

According to some other embodiments, the coupling agent is 4-(N-maleimidomethyl)cyclohexane carboxylic acid N-hydroxysuccinimide ester (SMCC), N-(3-dimethylaminopropyl)-N-ethyl carbodiimide hydrochloride (EDC), N-hydroxysulfosuccinimide sodium salt (Sulfo-NHS), or 3-(2-pyridyldithio)propionic acid N-hydroxysuccinimide ester (SPDP).

According to some other embodiments, the oily shell further comprises a hydrophobic drug.

According to some other embodiments, the aqueous core further comprises a hydrophilic drug.

In another aspect, a single-emulsion method of preparing the antibody-conjugated double-emulsion nanocapsules above is provided. First, an aqueous solution comprising the linking polyvinyl alcohol having the linking group but not comprising other polymers or other surfactants is prepared. An organic solution comprising the hydrophobic magnetic nanoparticles is also prepared. The aqueous solution and the organic solution are mixed to form an emulsion solution comprising double-emulsion nanocapsules. The organic solvent used by the organic solution is subsequently removed to obtain the double-emulsion nanocapsules. A first dispersion solution comprising the double-emulsion nanocapsules and a second dispersion solution comprising the antibody bonded with the coupling agent are respectively prepared. The first dispersion solution and the second dispersion solution are mixed to chemically react the liking group with the coupling agent to obtain the antibody-conjugated double-emulsion nanocapsules.

According to some embodiments, wherein the hydrophilic drug may be added into the aqueous solution.

According to some other embodiments, wherein the hydrophobic drug may be added into the organic solution.

In another aspect, a double emulsifying method of preparing the antibody-conjugated double-emulsion nanocapsules above is provided. A first aqueous solution comprising polyvinyl alcohol but not comprising other polymers or other surfactants and an organic solution comprising the hydrophobic magnetic nanoparticles are respectively prepared. The first aqueous solution and the organic solution are mixed to form a first emulsion solution, and the first emulsion solution is a water-in-oil emulsion solution. A second aqueous solution comprising a linking polymer having a linking group but not comprising other polymers or other surfactants is then prepared. The first emulsion solution and the second aqueous solution are mixed to form a second emulsion solution comprising double-emulsion nanocapsules. The organic solvent used by the organic solution is then removed to obtain the double-emulsion nanocapsules. A first dispersion solution comprising the double-emulsion nanocapsules and a second dispersion solution comprising the antibody bonded to the coupling agent are respectively prepared. The first dispersion solution and the second dispersion solution are mixed to chemically react the liking group with the coupling agent to obtain the antibody-conjugated double-emulsion nanocapsules.

According to some embodiments, wherein the hydrophilic drug may be added into the first aqueous solution.

According to some other embodiments, wherein the hydrophobic drug may be added into the organic solution.

It is to be understood that both the foregoing general description and the following detailed description are by examples, and are intended to provide further explanation of the invention as claimed.

The foregoing presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later. Many of the attendant features will be more readily appreciated as the same becomes better understood by reference to the following detailed description considered in connection with the accompanying drawings.

BRIEF DESCRIPTION OF THE DRAWINGS

FIGS. 10A and 10B were IVIS images of the nude mice experiments on the first day and the third day.

FIG. 11 shows volumes of the solid tumor varied at different times.

DETAILED DESCRIPTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

Antibody-Conjugated Double-Emulsion Nanocapsules

Figure 1A:
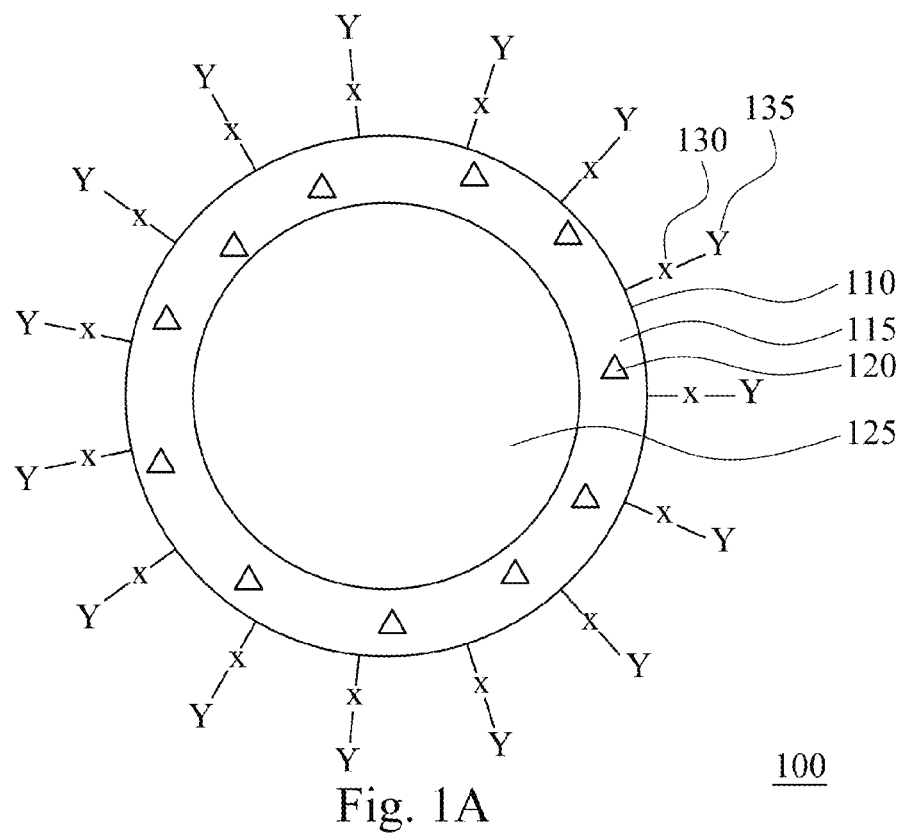
FIG. 1A is a cross-sectional diagram of an antibody-conjugated double-emulsion nanocapsule according to some embodiments of this disclosure.

FIG. 1A is a cross-sectional diagram of an antibody-conjugated double-emulsion nanocapsule according to some embodiments of this disclosure. In FIG. 1A, the antibody-conjugated double-emulsion nanocapsule 100 is formed from an oily shell 110 enclosing an aqueous core 125. The composition of the oily shell 110 includes a polymer 115 and hydrophobic magnetic nanoparticles 120. The surface of the oily shell 110 has linking groups 130 and antibody 135 bonded to the linking groups 130 via a coupling agent (not shown in FIG. 1A). The diameter of the antibody-conjugated double-emulsion nanocapsule 100 is about 50 nm to about 400 nm.

The polymer 115 includes at least a linking polyvinyl alcohol, which is modified from polyvinyl alcohol (PVA) to have the liking groups 130, or a combination of polyvinyl alcohol and a linking polymer having the linking groups 130. Furthermore, it is emphasized that the composition of the oily shell 110 does not need to include any other surfactants or other polymers.

The polyvinyl alcohol or the linking polyvinyl alcohol itself can turn the hydrophilic group toward the aqueous core 125 inside the oily shell 110 and the aqueous solution outside the oily shell 110. Therefore, the inner water-oil interface and the outer oil-water interface of the oily shell 110 can be simultaneously stabilized without using any other surfactants or any other polymers.

The linking group 130 above may be a carboxylic group, a thiol group, an aldehyde group, an amine group, or a hydroxyl group. For example, the linking polyvinyl alcohol above may be carboxymethylated polyvinyl alcohol (CMPVA), thiolated polyvinyl alcohol (TPVA), or a copolymer of PVA-TPMAA. The linking polymer above may be polyacrylic acid (PAA), polymethacrylic acid (PMAA), carboxymethylated polyvinyl alcohol (CMPVA), thiolated polyvinyl alcohol (TPVA), thiolated polymethacrylic acid (TPMAA), or a copolymer of PVA-TPMAA.

The chemical structures of the PAA, PMAA, CMPVA, TPVA, and TPMAA are listed in the table 1 below.

TABLE 1

Exemplified linking polymers, including linking PVAs

| Structure | Name |
|---|---|
| $-[\text{CH}_2-\text{CH}(\text{COOH})]_n-$ | PAA |
| $-[\text{CH}_2-\text{C}(\text{CH}_3)(\text{COOH})]_n-$ | PMAA |
| $-[\text{CH}_2-\text{CH}(\text{OH})]_x-[\text{CH}_2-\text{CH}(\text{OCH}_2\text{COOH})]_y-$ | CMPVA |

TABLE 1-continued

Exemplified linking polymers, including linking PVAs

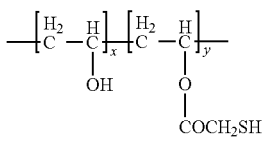  TPVA

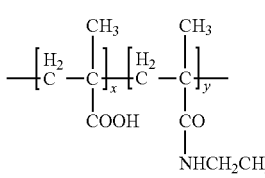  TPMAA

The antibody 135 may be any needed antibody. The selection of the antibody depends on the antigen needed to be bound. For example, the coupling agent-antibody conjugate 135 may be breast cancer antibody trastuzumab (commercial name is Herclon or Herceptin), colorectal cancer antibody cetuximab, epidermal growth factor receptor antibody panitumumab, or angiogenesis inhibitor antibody bevacizumab.

The hydrophobic magnetic nanoparticles 120 may be nanoparticles having a hydrophobic functional groups-modified surface and made from $Fe_2O_3$, $Fe_3O_4$, $CoFe_2O_4$, or $MnFe_2O_4$. The hydrophobic functional group may be a long-chained alkyl group or a long-chained alkenyl group, such as oleic acid or oleylamine. The hydrophobic paramagnetic nanoparticles 120 can stabilize the oily shell 110 to prevent the oily shell 110 from collapsing. In addition to being a contrast agent of magnetic resonance imaging (MRI), the hydrophobic paramagnetic nanoparticles 120 also can be used to locally heat and then break the oily shell 110 by magnetic fluid hyperthermia (MFH) under a high frequency magnetic field (HFMF).

Since the double-emulsion nanocapsule 100 has the oily shell 110 and the aqueous core 125 to respectively accommodate a hydrophobic drug and a hydrophilic drug therein, the double-emulsion nanocapsule 100 can be used as a drug carrier of the hydrophobic drug, the hydrophilic drug, or a combination thereof. Furthermore, the release rate of a drug can be controlled by the strength and on/off state of an applied external alternative magnetic field.

Figure 1B:
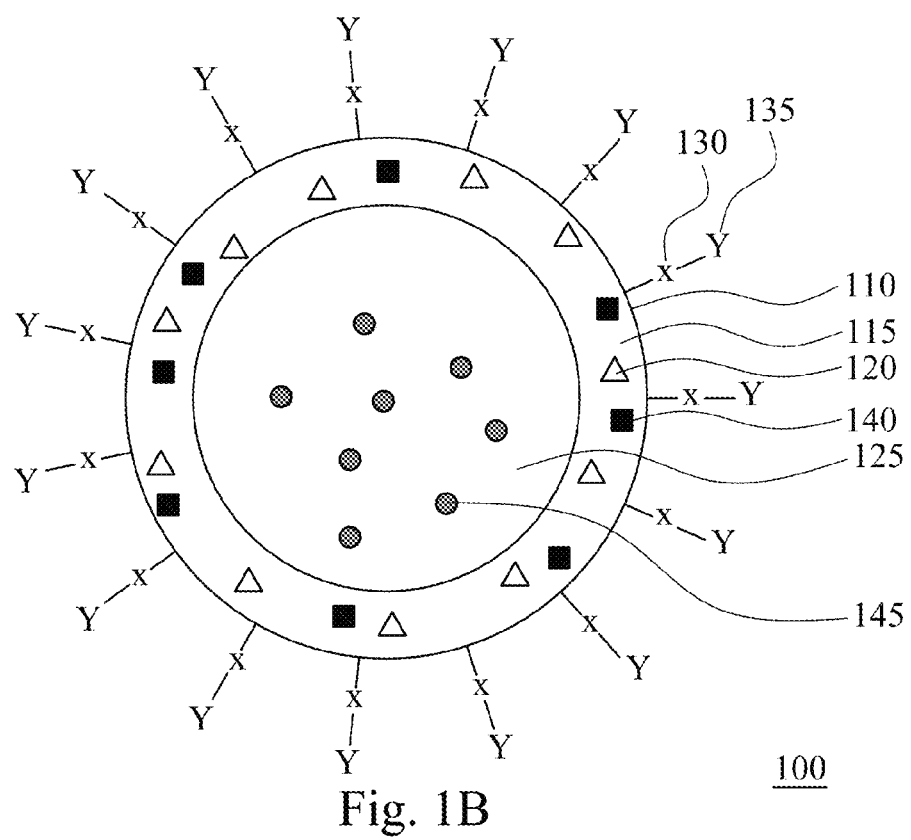
FIG. 1B is a cross-sectional diagram of a double-emulsion nanocapsule in FIG. 1A used as a drug carrier according to some other embodiments of this disclosure.

FIG. 1B is a cross-sectional diagram of a double-emulsion nanocapsule in FIG. 1A used as a drug carrier according to some other embodiments of this disclosure. In FIG. 1B, a hydrophilic drug 145 is accommodated in the aqueous core 125 of the double-emulsion nanocapsule 100. A hydrophobic drug 140 is accommodated in the oily shell 110 of the double-emulsion nanocapsule 100. For example, the hydrophilic drug 145 may be doxorubicinl (DOXO) or cisplatin, and the hydrophobic drug 140 may be paclitaxel (PTX), docetaxel (Dtxl), camptothecin (CPT), or cururmine.

Preparation Method of Antibody-Conjugated Double-Emulsion Nanocapsule

The preparation method of antibody-conjugated double-emulsion nanocapsules includes two stages. At the first stage, double-emulsion nanocapsules having linking groups are prepared by a single emulsifying method or a double emulsifying method. At the second stage, the obtained double-emulsion nanocapsules are reacted with antibody to form antibody-conjugated double-emulsion nanocapsules.

Figure 2A:
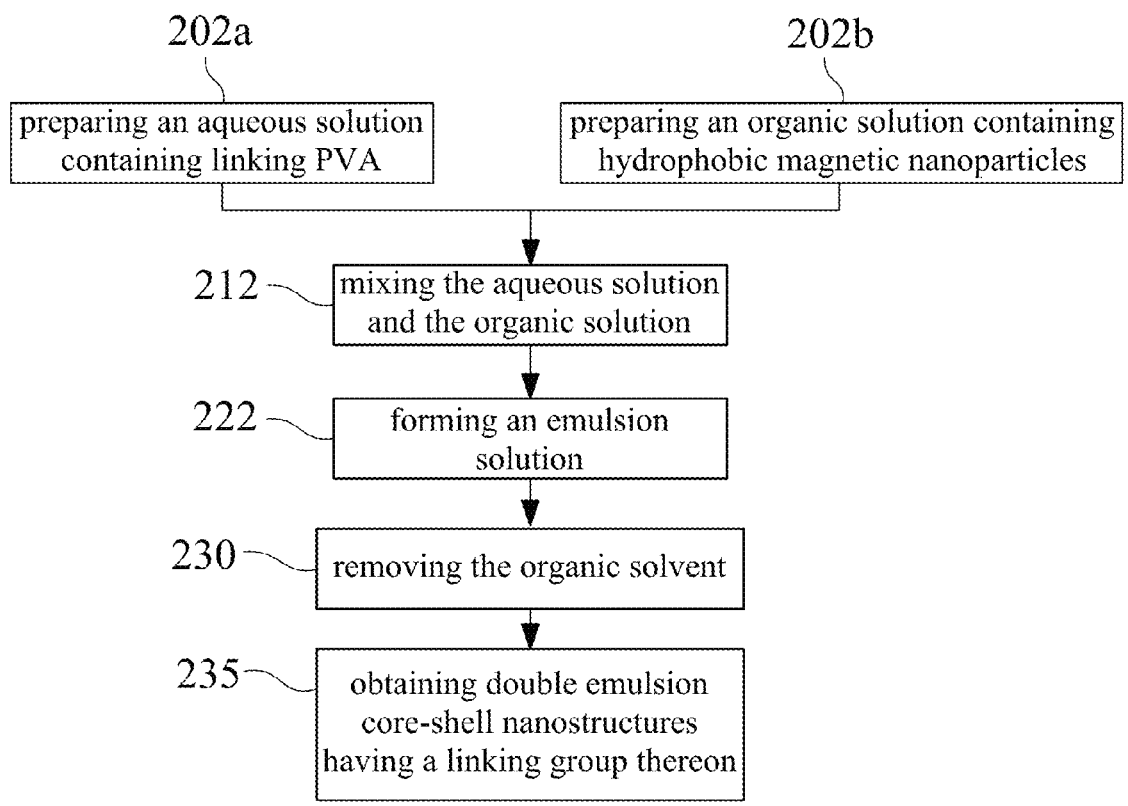
FIG. 2A is a flow chart of the single emulsifying method for preparing double-emulsion nanocapsules having linking groups thereon according to some embodiments of this disclosure.

FIG. 2A is a flow chart of the single emulsifying method for preparing double-emulsion nanocapsules having linking groups thereon according to some embodiments of this disclosure. In FIG. 2A, an aqueous solution containing linking PVA (step 202a) and an organic solution containing hydrophobic magnetic nanoparticles (step 202b) are respectively prepared. The aqueous solution and the organic solution are then mixed (step 212) to form an emulsion solution (step 222). The organic solvent in the emulsion solution is then removed (step 230) to obtain double-emulsion nanocapsules having linking groups (step 235).

In the step 202a above, a hydrophilic drug may be further added into the aqueous solution. In the step 202b above, a hydrophobic drug may be further added into the organic solution.

When the organic solution contains only the hydrophobic magnetic nanoparticles, the organic solvent is better to have the properties of effectively dissolving or dispersing the hydrophobic magnetic nanoparticles, immiscible with water, and lower boiling point. When the organic solution further contains a hydrophobic drug, the organic solvent is better to further have the property of effectively dissolving or dispersing the hydrophobic drug.

The reason for choosing an organic solvent with a lower boiling point is that the organic solvent can be easily removed without over-heating to prevent the outer shape of the double-emulsion nanocapsules from being influenced by non-controllable adverse effects. The boiling point of the organic solvent can be lower than 90° C. The organic solvent can be chloroform, dichloromethane, trichloroethane, or acetonitrile, for example.

In the step 212 above, the method of mixing may be ultrasound sonication, for example. In step 230 above, the method of removing the organic solvent may be volatilization at room temperature or reduced pressure distillation.

Figure 2B:
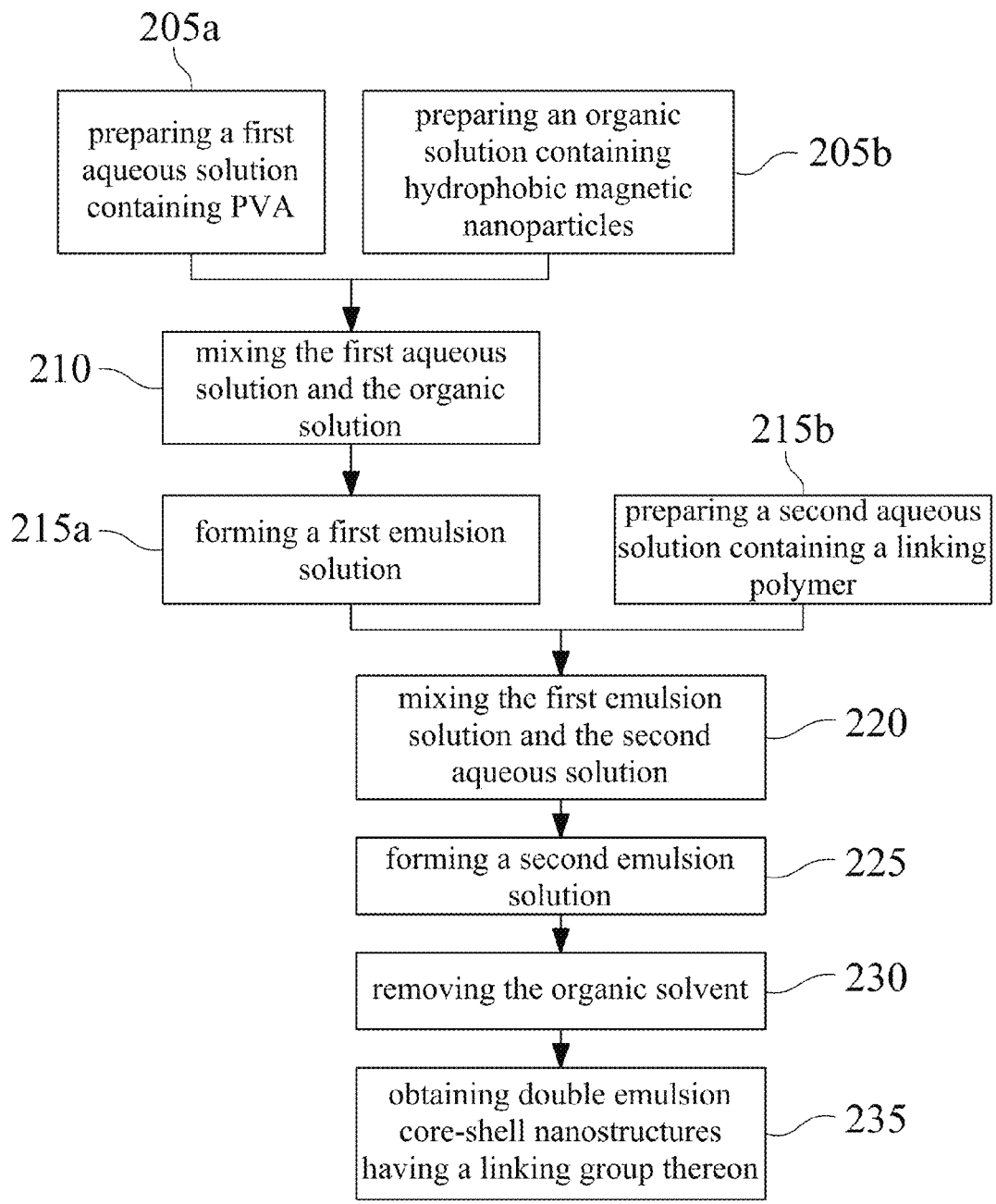
FIG. 2B is a flow chart of the double emulsifying method for preparing double-emulsion nanocapsules having linking groups according to some other embodiments of this disclosure.

FIG. 2B is a flow chart of the double emulsifying method for preparing double-emulsion nanocapsules having linking groups according to some other embodiments of this disclosure. In FIG. 2B, a first aqueous solution containing PVA (step 205a) and an organic solution containing hydrophobic magnetic nanoparticles (step 205b) are respectively prepared. A small amount of the first aqueous solution and a large amount of the organic solution are mixed (step 210) to form a first emulsion solution (step 215a), which is a water-in-oil emulsion solution. This is the first emulsifying stage.

In step 205a above, a hydrophilic drug may be further added in to the first aqueous solution. In step 205b above, a hydrophobic drug may be further added into the organic solution. The selection of the organic solvent for the organic solution in step 205b is the same as the step 202b in FIG. 2A, and hence omitted here.

A second aqueous solution containing a linking polymer is then prepared (step 215b). The first emulsion solution and the second aqueous solution are mixed (step 220) to form a second emulsion solution (step 225). This is the second emulsifying stage.

The mixing method of step 210 and step 220 above may be ultrasound sonication, for example. In step 230 above, the method of removing the organic solvent may be volatilization at room temperature or reduced pressure distillation.

Figure 2C:
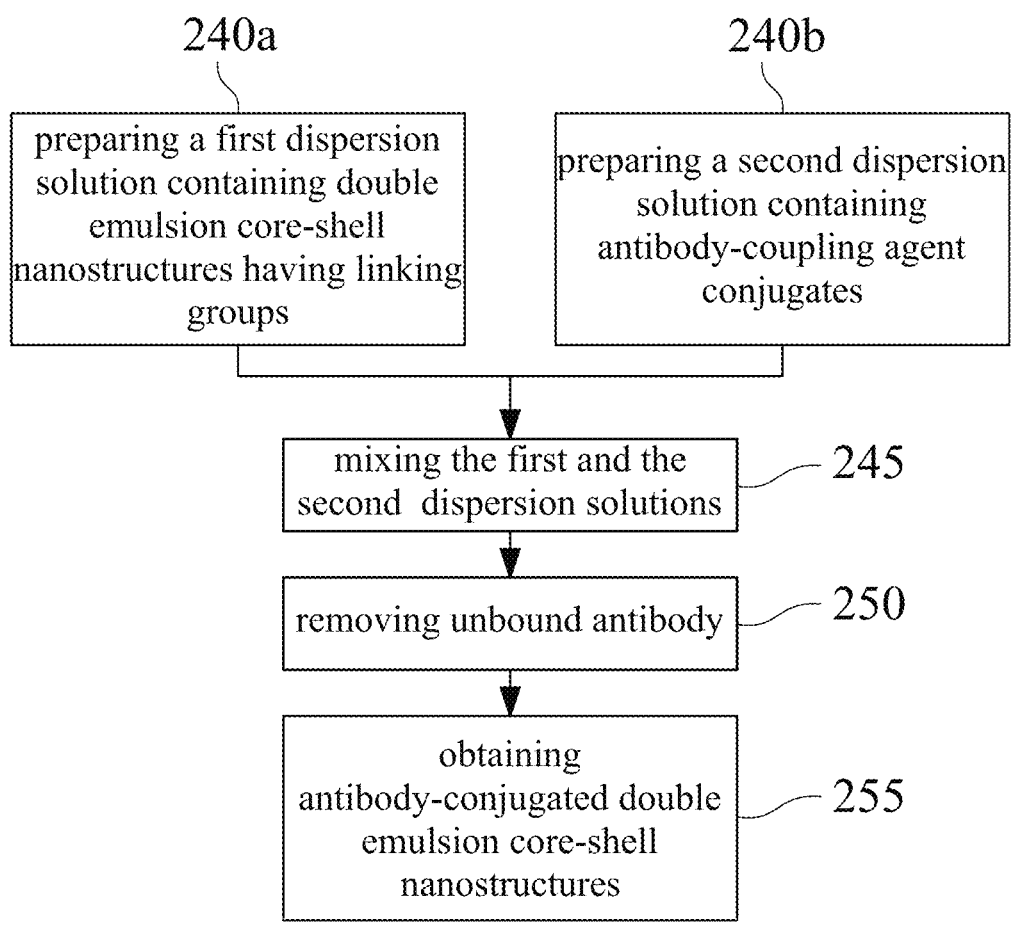
FIG. 2C is a flow chart of a method for reacting an antibody-coupling agent conjugate and the double-emulsion nanocapsules having linking groups according to some embodiments of this disclosure.

FIG. 2C is a flow chart of a method for reacting an antibody-coupling agent conjugate and the double-emulsion nanocapsules having linking groups according to some embodiments of this disclosure. In FIG. 2C, a first dispersion solution containing double-emulsion nanocapsules (step 240a) and a second dispersion solution containing antibody-coupling agent conjugates (step 240b) are respectively prepared. The first and the second dispersion solutions are mixed (step 245) to react the antibody-coupling agent conjugates with the linking groups on the double-emulsion nanocapsules. Next, the unbound antibody is removed by centrifugation (step 250) to obtain antibody-conjugated double-emulsion nanocapsules (step 255).

Usually, the antibody uses a free primary amine group to connect with a coupling agent to form an antibody-coupling agent conjugate. According to some embodiments, some suitable coupling agents for forming the antibody-coupling agent conjugates above are listed in Table 2 below. For example, when the linking group above is a thiol group, the coupling agent may be SMCC or SPDP. When the linking group of the linking polymer used in the double emulsifying method above is a carboxylic group, the coupling agent may be a combination of EDC and sulfo-NHS.

The selection of the solvents for the first dispersion solution (step 240a) and the second dispersion solution (step 240b) depends on the coupling agent used. For example, if SMCC is used as the coupling agent, phosphate buffered saline (PBS) solution, which contains 0.1 M $Na_3PO_4$ and 0.15 M NaCl and pH value is 7.4, may be used. If EDC and sulfo-NHS are used as the coupling agent, MES buffer solution containing 0.1 M 2-(N-morpholino)ethanesulfonic acid (MES) and 0.5 M NaCl and pH value is 6.0, may be used.

In the embodiments described below, "double-emulsion nanocapsule" is abbreviated as "DENC," and "antibody-conjugated double-emulsion nanocapsule" is abbreviated as "antibody-DENC" to simplify the writing.

TABLE 2

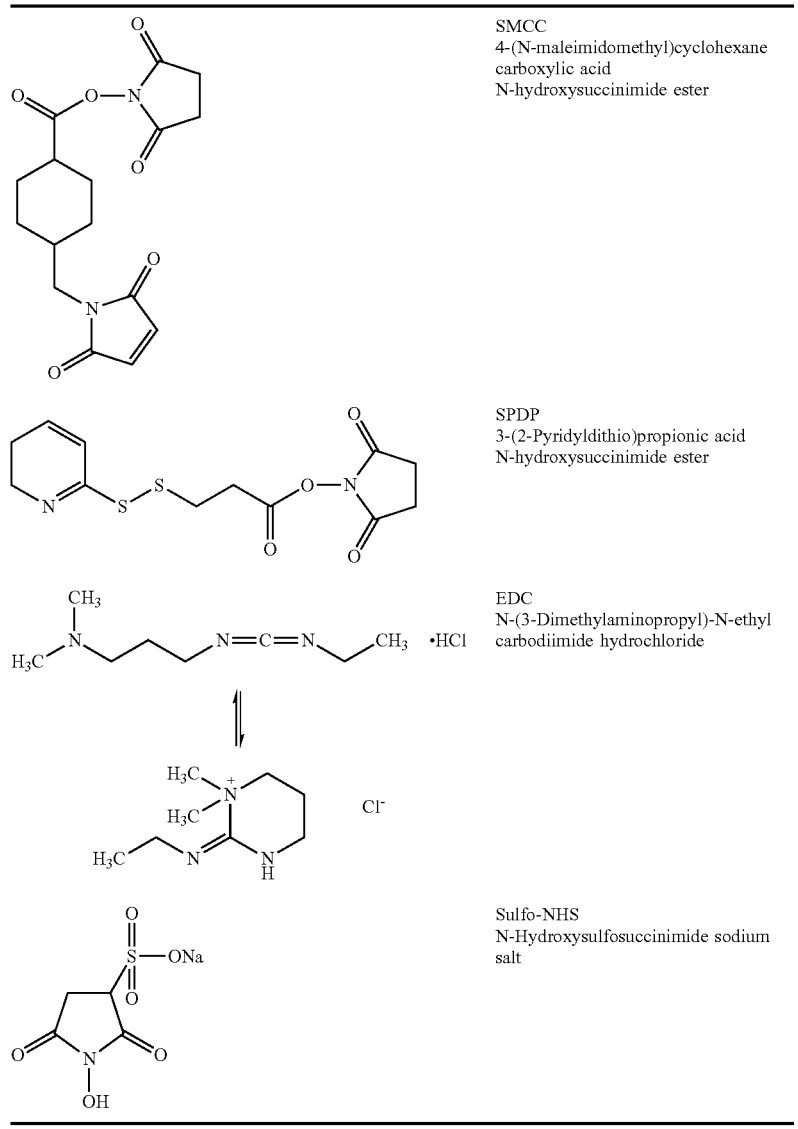

| | |
|---|---|
| | SMCC<br>4-(N-maleimidomethyl)cyclohexane carboxylic acid<br>N-hydroxysuccinimide ester |
| | SPDP<br>3-(2-Pyridyldithio)propionic acid<br>N-hydroxysuccinimide ester |
| | EDC<br>N-(3-Dimethylaminopropyl)-N-ethyl carbodiimide hydrochloride |
| | Sulfo-NHS<br>N-Hydroxysulfosuccinimide sodium salt |

Embodiment 1

Preparing Fe₃O₄ Nanoparticles Covered with Oleic Acid

In this embodiment, $Fe_3O_4$ nanoparticles covered with oleic acid (abbreviated as IO-OA nanoparticles) with a diameter of about 5 nm was prepared. The exemplified preparation method of IO-OA nanoparticles is described below. Furthermore, the preparation method of IO-OA nanoparticles may refer to Sun, S. H.; Zeng, H.; Robinson, D. B.; Raoux, S.; Rice, P. M.; Wang, S. X.; Li, G. X. Journal of the American Chemical Society, 2004, 126, (1), 273-279, which is incorporated herein by reference.

0.708 g of Fe(acac)₃, 2.58 g of 1,2-Hexadecanediol, 0.565 g of oleic acid, 0.535 g of oleylamine, 20 mL of benzyl ether were added into a three-necked flask. The mixture above was heated, under a condition of nitrogen atmosphere and cycled cooling water, respectively at 100° C. for 30 minutes, 200° C. for 60 minutes, and 285° C. for 30 minutes to form IO-OA nanoparticles. Next, the obtained IO-OA nanoparticles were dispersed in ethanol and then centrifuged at 6000 rpm to remove the upper solution. After repeating for several times, the obtained IO-OA nanoparticles were stored in ethanol.

Embodiment 2

Preparing Thiolated Polymethacrylic Acid

In this embodiment, thiolated polymethacrylic acid (TPMAA) was prepared. The exemplified preparation method is described below, and the synthesis scheme I is also referred at the same time.

Synthesis Scheme I

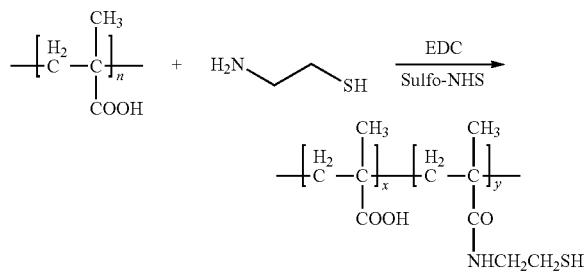

250 mg of aqueous solution containing 30 wt % of PMAA was sequentially added with 5 mL of pH 8 PBS solution, 75 mg of catalyst EDC, and 40 mg of catalyst sulfo-NHS. After mixing and stirring for 15 minutes, 5 mg of cysteamine was then added. The mixture was stirred until the next day to react the primary amine group of the cysteamine with the carboxylic group of the PMAA to form amide bond and obtain TPMAA. Dialysis was used to remove catalyst EDC and sulfo-NHS, and water was then removed by freeze dry to obtain TPMAA crystals.

Embodiment 3

Preparing PVA-TPMAA Copolymer

In this embodiment, PVA-TPMAA copolymer was prepared. The exemplified preparation method is described below.

PVA and TPMAA obtained above were mixed. Concentrated sulfuric acid was then added to form PVA-TPMAA copolymer and side product of water. Next, saturated sodium carbonate was used to separate PVA-TPMAA copolymer and reactants of TPMAA and PVA to obtain the product of PVA-TPMAA copolymer.

Embodiment 4

Preparing Thiolated Polyvinyl Alcohol

In this embodiment, thiolated polyvinyl alcohol (TPVA) was prepared. The exemplified preparation method was described below, and the synthesis scheme II below was referred at the same time. The reference for the preparation of TPVA is Gupta B, Anjum S and Ikram S. Preparation of thiolated polyvinyl alcohol hydrogels. *Journal of Applied Polymer Science.* 2013; 129: 815-21.

Synthesis Scheme II

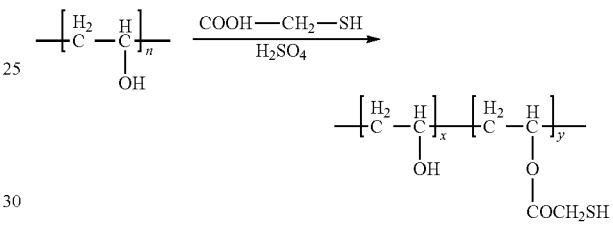

$n = x + y$

PVA was dissolved in deionized water to form 2 wt % of PVA aqueous solution. 20-99% (v/v) of thioglycolic acid and 0.1-1 wt % of sulfuric acid aqueous solution were slowly added into the PVA aqueous solution. The mixture was heated in an oil bath to perform an esterification reaction. Next, methanol was slowly poured into the PVA esterification solution to form precipitate. The precipitate was collected and purified for several times by methanol to obtain powder. The powder was then freeze dried to obtain TPVA white crystal powder.

Embodiment 5

Preparing Carboxymethylated Polyvinyl Alcohol

In this embodiment, carboxymethylated polyvinyl alcohol (CMPVA) was prepared, and the exemplified method was described below. Synthesis scheme III is referred at the same time. The reference for the preparation of CMPVA is Yu C. and Li B. Preparation and characterization of carboxymethyl polyvinyl alcohol-graphite nanosheet composites. *Polymer Composites.* 2008; 29: 998-1005.

Synthesis Scheme III

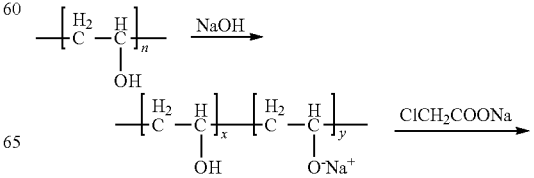

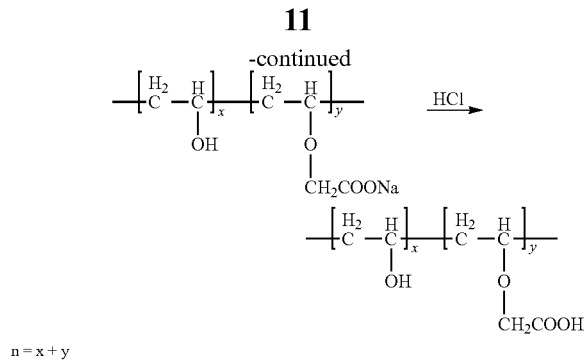

n = x + y

First, NaOH was added into 2 wt % of PVA aqueous solution to activate the —OH group of PVA. Chloroacetic acid (ClCH₂COOH) was dissolved in ethanol and neutralized by NaOH to form an ethanol solution of sodium chloroacetate (ClCH₂COONa). The two solutions above were mixed to form a sodium salt of CMPVA. After 5 hours, appropriate amount of HCl was added to adjust the pH value to 6. Subsequently, excess amount of alcohol was added to purify CMPVA. The ethanol purification step was repeated for several times.

Embodiment 6

Preparation of Antibody-DENC Containing PVA/TPMAA Mixture

In this embodiment, DENC containing PVA/TPMAA mixture was prepared by using the double emulsifying method in FIG. 2B. The drug used included hydrophilic doxorubicin (Dox) and cisplatin, and hydrophobic paclitaxel (PTX) and camptothecin (CPT). The antibody was then bound to the DENC containing PVA/TPMAA mixture by using the method of FIG. 2C.

A first aqueous solution of a hydrophilic drug and PVA, a CHCl₃ solution of a hydrophobic drug and IO-OA nanoparticles, and a second aqueous solution of PVA and TPMAA were respectively prepared. In the first aqueous solution of the hydrophilic drug and PVA, the concentration of the PVA was 20 mg/mL, the concentration of the hydrophilic drug (doxorubicin or cisplatin) was 8 mg/mL. In the CHCl₃ solution of the hydrophobic drug and the IO-OA nanoparticles, the concentration of the IO-OA nanoparticles was 20 mg/mL, as well as the concentration of paclitaxel was 30 mg/mL when the hydrophobic drug was paclitaxel, and the concentration of camptothecin was 5 mg/mL when the hydrophobic drug was camptothecin. In the second aqueous solution of PVA and TPMAA, the concentration of PVA was 20 mg/mL, and the concentration of TPMAA was 2 mg/mL. The average molecular weight of the PVA used was respectively 16,000, 25,000, 31,000, and 47,000. In TPMAA, about 37% of the carboxylic group was modified to have a thiol group.

0.2 mL of the first aqueous solution containing the hydrophilic drug and PVA, as well as 0.5 mL of the CHCl₃ solution containing the IO-OA nanoparticles and the hydrophobic drug were mixed and emulsified by ultrasound sonication at a frequency of 20 kHz. After the emulsifying, 1.5 mL of the second aqueous solution containing PVA and TPMAA was further added, and the mixture was emulsified again by ultrasound sonication at 20 kHz to obtain DENCs containing PVA/TPMAA mixture. The volatile CHCl₃ was removed by placing the final obtained emulsion solution at an open space to evaporate the CHCl₃. The temperature of evaporating the CHCl₃ may change the morphology of the DENCs. Next, the DENCs containing PVA/TPMAA mixture were dispersed in 3 mL of PBS solution containing 0.1 M of sodium phosphate and 0.15 M of NaCl.

When only one drug was encapsulated by the DENCs above, the encapsulation efficiency and the diameter of the DENCs are listed in table 3 below. From table 3, it can be known that the encapsulation efficiency of the hydrophobic drugs was usually greater than the encapsulation efficiency of the hydrophilic drug. Therefore, the diameter of the DENCs encapsulating the hydrophobic drugs was usually larger. Besides, the encapsulation efficiency of the hydrophilic drugs was more than 75%, which is quite good for using the double emulsifying method to prepare the DENCs encapsulating the hydrophilic drugs.

TABLE 3

Encapsulating efficiency of single hydrophilic drug or single hydrophobic drug

| Encapsulated drug | | Encapsulating efficiency (%) | Carrier diameter (nm) |
|---|---|---|---|
| Hydrophobic drug | paclitaxel | 95 | 138 |
| | camptothecin | 91 | 133 |
| Hydrophilic drug | cisplatin | 76 | 131 |
| | doxorubicin | 83 | 130 |

Figure 3:
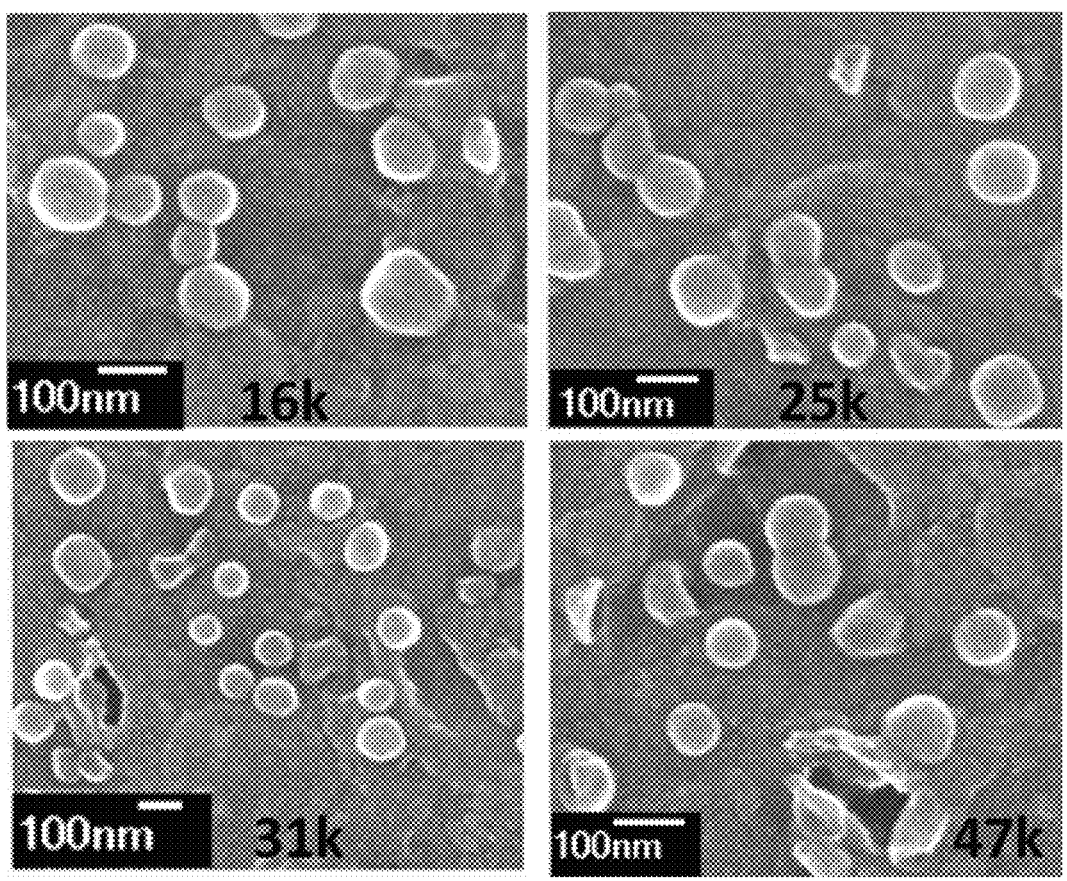
FIG. 3 is scanning electron microscopic (SEM) images of the vacant DENCs using various PVAs having various average molecular weights.

FIG. 3 is scanning electron microscopic (SEM) images of the vacant DENCs using various PVAs having various average molecular weights. In FIG. 3, the average molecular weights of PVA contained in the vacant DENCs were 16000, 25000, 31000, and 47000, respectively. The vacant DENCs did not encapsulate drugs. From FIG. 3, the greater the average molecular weight of the PVA was, the smaller the diameter of the vacant DENCs was.

Next, 1 mg of breast cancer antibody trastuzumab and 4.8 mg of coupling agent SMCC were respectively dissolved in 2 mL and 5 mL of PBS solutions containing 0.1 M of sodium phosphate and 0.15 M of NaCl and then mixed together. The mixture was reacted at 4° C. for 2 hours to obtain trastuzumab-SMCC conjugate, and then centrifuged at 8000 rpm to remove unreacted SMCC. The trastuzumab-SMCC conjugate was then re-dispersed in 1 mL of PBS solution containing 0.1 M of sodium phosphate and 0.15 M of NaCl.

The dispersion solutions of the DENCs and the trastuzumab-SMCC conjugates were mixed and reacted at 4° C. for 2 hours. After centrifugation, the unreacted trastuzumab-SMCC conjugate was removed, and the product of trastuzumab-DENCs was re-dispersed in 4 mL of deionized water.

The coupling agent SMCC became a bridge to link the —SH linking group of TPMAA with the —NH₂ group of the breast cancer antibody of trastuzumab. Hence, trastuzumab was bound on the outer surface of the oily shell of the DENCs through SMCC and the thiol group of TPMAA.

Figure 4A:
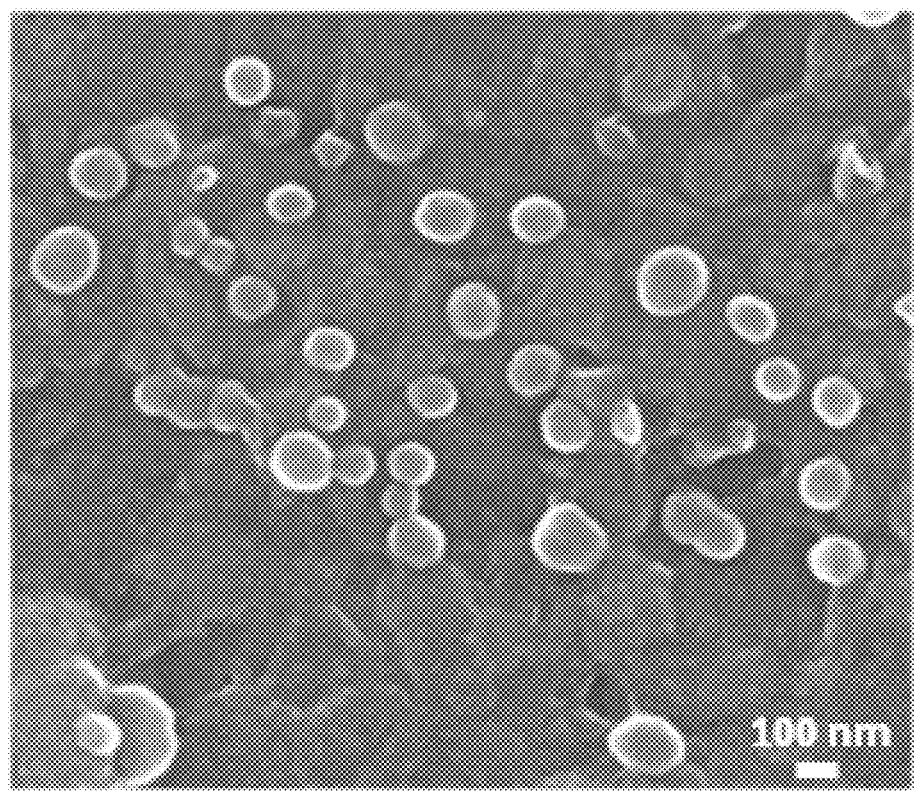
FIGS. 4A and 4B are SEM images of vacant DENCs before and after linking the breast cancer antibody of trastuzumab.
Figure 4B:
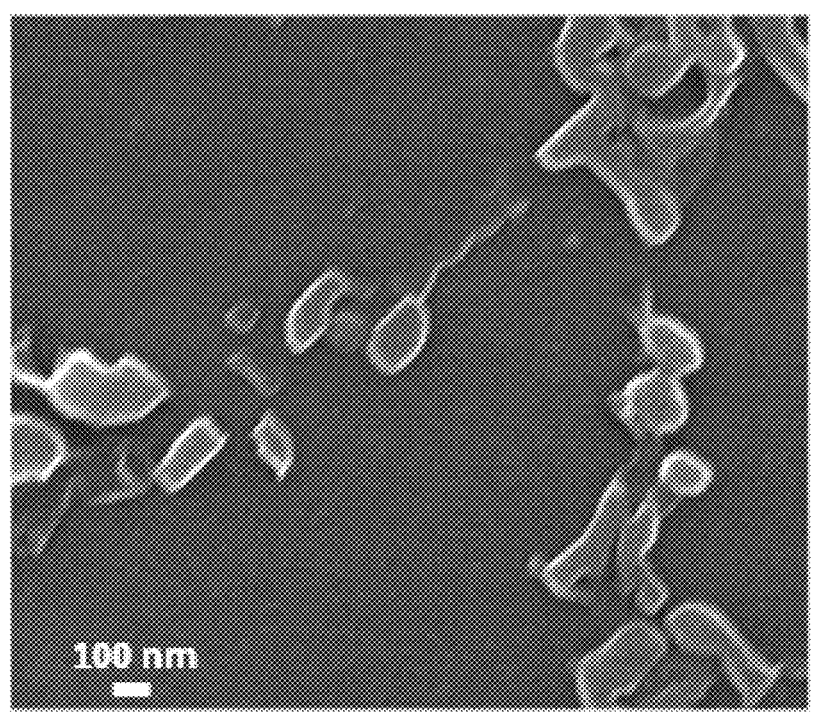

FIGS. 4A and 4B are SEM images of vacant DENCs before and after linking the breast cancer antibody of trastuzumab. The PVA used had an average molecular weight of 16000. In FIG. 4A, the vacant DENCs containing TPMAA/PVA mixture had been washed by deionized water, re-dispersed in deionized water, and then freeze dried. The vacant DENCs still maintain the hollow spherical structure. In FIG. 4B, the vacant DENCs in FIG. 4A were bound to trastuzumab-SMCC conjugate. Since the surface of the vacant DENCs was modified by trastuzumab-SMCC conjugate, the morphology of the trastuzumab-DENCs was changed.

Embodiment 7

Effect of pH Values of Solutions on Release of Drugs Encapsulated in DENCs Containing PVA/TPMAA Mixture In this embodiment, the effect of pH values of solutions on the release of drugs encapsulated in antibody-DENCs containing PVA/TPMAA mixture was tested. The oily shell was composed of PVA having a molecular weight of 16000 and TPMAA. The drug used included hydrophilic doxorubicin (Dox) and hydrophobic paclitaxel (PTX).

TPMAA is a modified PMAA polymer having thiol functional groups, and PMAA is a pH-sensitive polymer. The carboxylic acid groups and methyl groups on side chains of PMAA are the main factors affecting PMAA to show different appearance in various environments having various pH values. In a neutral environment, PMAA is randomly coiled and hydrophilic. In an acid environment, PMAA is transformed and shrunk to a globule-like structure and becomes hydrophobic. It was hoped that the pH-sensitive property of PMAA can be preserved after being modified by thiol groups for linking breast cancer antibody of trastuzumab. Therefore, DENCs encapsulating dual drugs were respectively placed in a neutral environment (pH 7) and an acidic environment (pH 4) to observe the release amount of drugs.

Figure 5A:
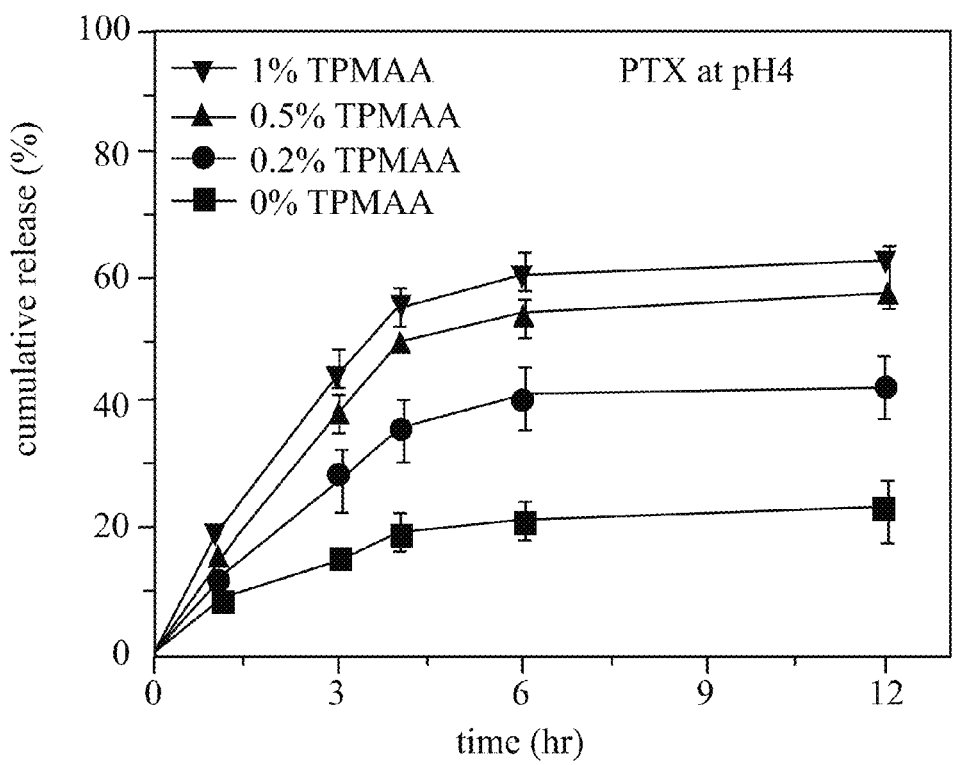
FIG. 5A shows drug release profiles of hydrophobic PTX encapsulated in DENCs containing various amounts of TPMAA at pH 4.
Figure 5B:
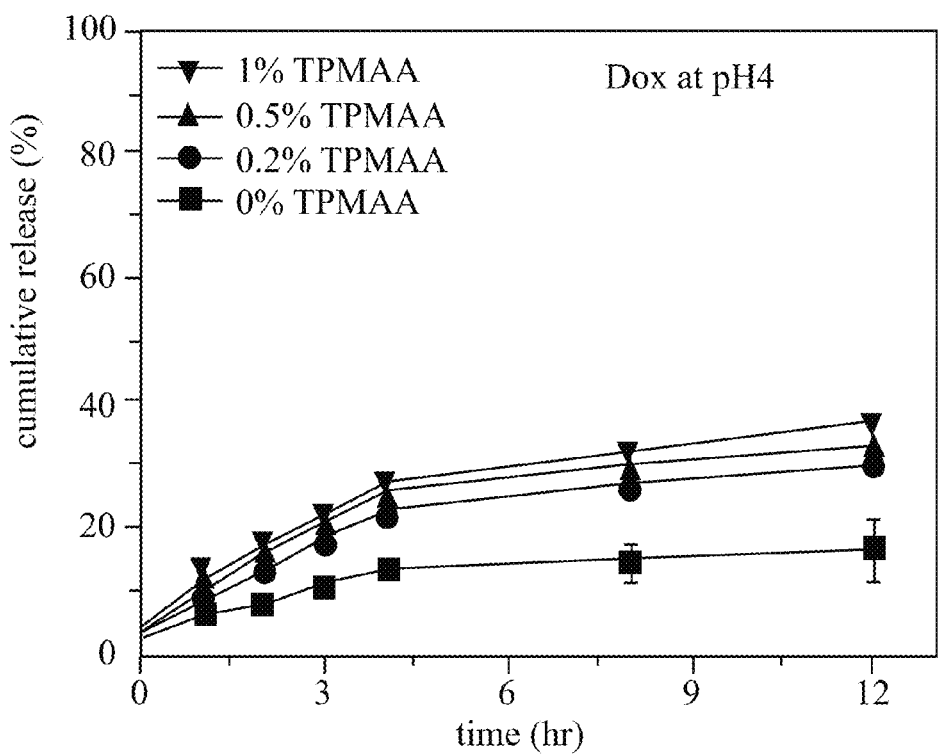
FIG. 5B shows drug release profiles of hydrophilic Dox encapsulated in DENCs containing various amounts of TPMAA at pH 4.

FIG. 5A shows drug release profiles of hydrophobic PTX encapsulated in DENCs containing various amounts of TPMAA at pH 4. FIG. 5B shows drug release profiles of hydrophilic Dox encapsulated in DENCs containing various amounts of TPMAA at pH 4. In FIGS. 5A and 5B, the modification percentage of TPMAA was 37%. From FIGS. 5A and 5B, it can be known that the addition amount of TPMAA was increased during the preparation process, the release amounts of PTX and Dox both were increased at the acidic environment at pH 4. This result shows that TPMAA may increase the release rate of drugs from the DENCs in an acidic environment.

Figure 5C:
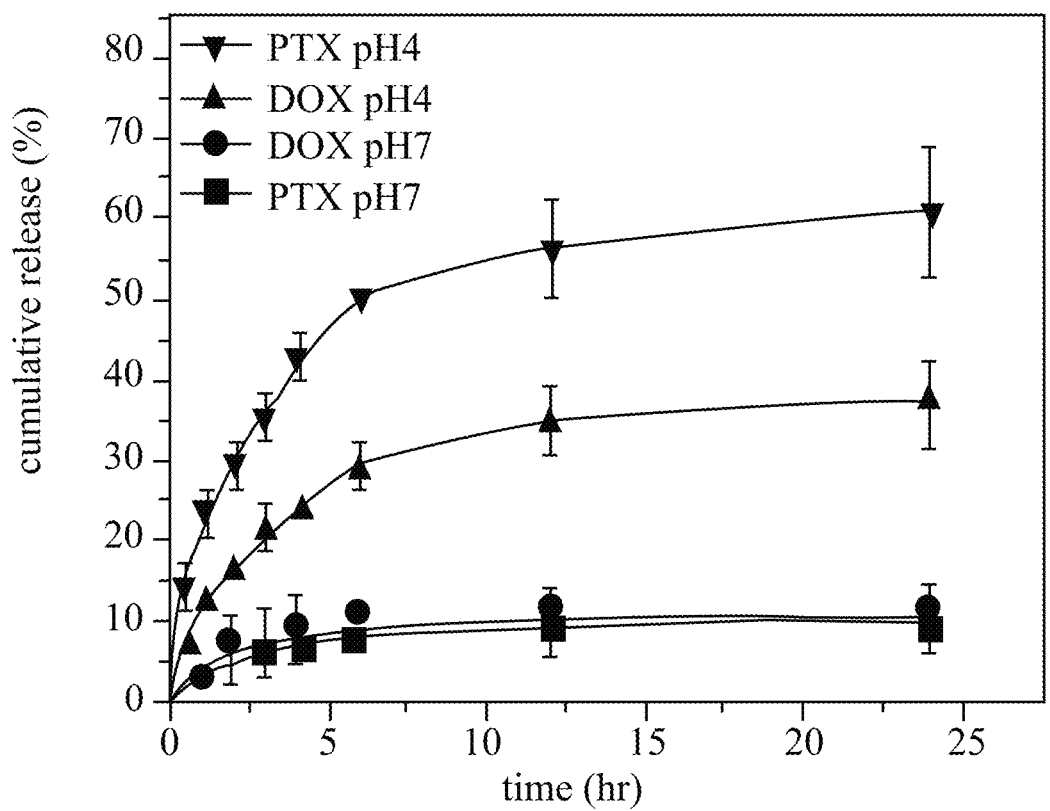
FIG. 5C shows drug release profiles of PTX and Dox both encapsulated in DENCs at pH 4 and pH 7.

FIG. 5C shows drug release profiles of PTX and Dox both encapsulated in DENCs at pH 4 and pH 7. In FIG. 5c, the modification percentage of TPMAA was 37%. The addition amount of TPMAA was 1 wt %. From FIG. 5C, it can be known that the release amounts of drugs at pH 4 are far greater than the release amounts of drugs at pH 7. In the acidic environment of pH 4, the release amount of the hydrophobic PTX was greater than the release amount of the hydrophilic Dox.

Figure 6A:
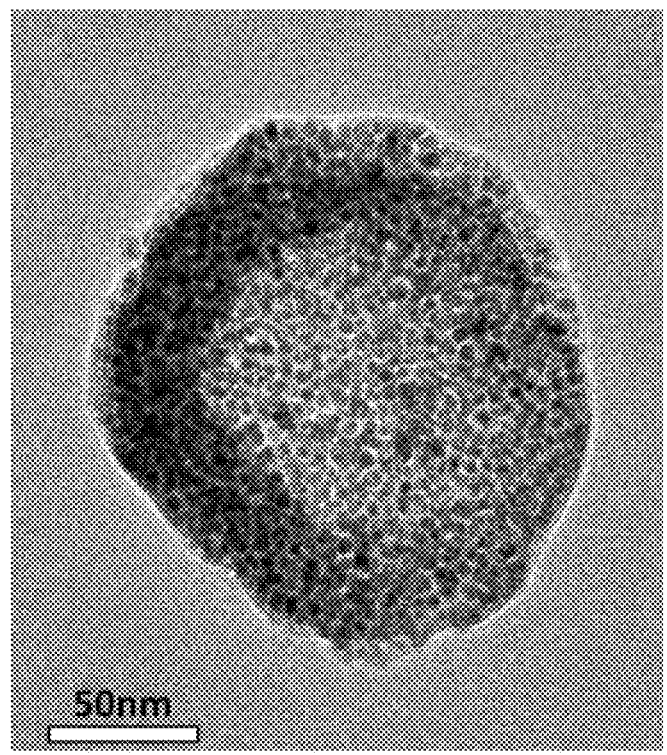
FIGS. 6A and 6B are transmission electron microscopic (TEM) images of trastuzumab-DENCs containing PVA/TPMAA mixture respectively at pH 7 and pH 4.
Figure 6B:
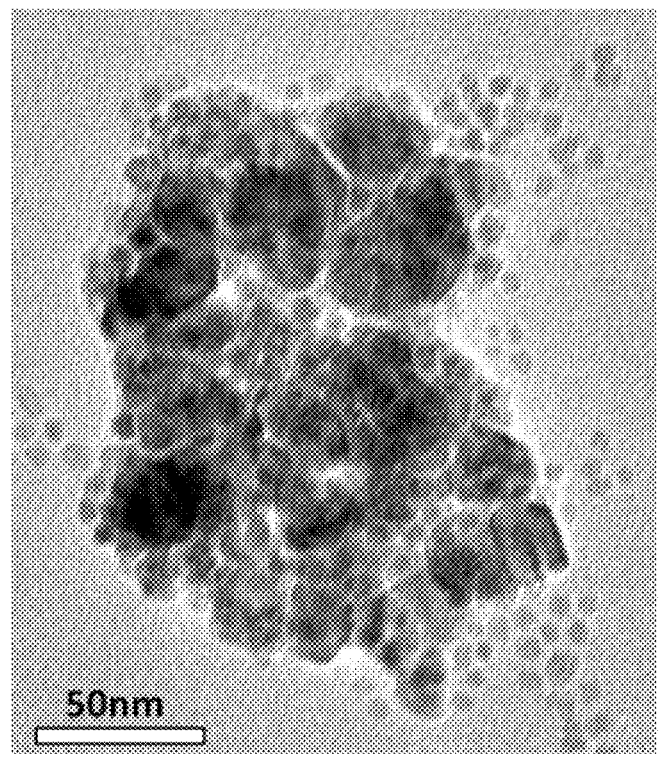

FIGS. 6A and 6B are transmission electron microscopic (TEM) images of trastuzumab-DENCs containing PVA/TPMAA mixture respectively at pH 7 and pH 4. The addition amount of TPMAA was 1 wt %, and the modification percentage of TPMAA was 37%. FIG. 6A shows that the trastuzumab-DENC had a spherical shell in the neutral environment. FIG. 6B shows that the shell of the trastuzumab-DENC was shrunk and deformed in the acidic environment.

The drug release behaviors above were consistent with that the TPMAA shrunk in an acidic environment and was transformed to be hydrophobic. When a lot of hydrogen ions are present in the environment, the TPMAA in the shell begins to shrink and the shell is thus deformed and extruded. Therefore, the hydrophobic drug located in the oily shell could be released more than the hydrophilic drug located in the aqueous core.

Embodiment 8

Recognition of Trastuzumab-Conjugated Carrier to HER-2 Overexpressing Cells

In this embodiment, whether the trastuzumab-DENC can target HER-2 overexpressing cells or not was verified. The selected HER-2 overexpressing cell clone was SkBr3 (human breast adenocarcinoma) cells. The shell of the tested trastuzumab-DENC was composed of a mixture of PVA having a molecular weight of 16000 and TPMAA. The addition amount of TPMAA was 1 wt %, and the modification percentage of TPMAA was 37%.

First, the DENCs encapsulating hydrophilic Dox were respectively conjugated with the breast cancer antibody trastuzumab and an antibody IgG, which is not specific to SkBr3 cells. Then, the antibody-DENCs encapsulating hydrophilic doxorubicin (Dox) and the SkBr3 cells were incubated together at 37° C. for 30 minutes. Since Dox can emit fluorescence (excited at a wavelength of 488 nm and emitting at a wavelength of 580 nm), flow cytometer can be used to detect the fluorescence intensity of Dox bound onto the cell surface of the SkBr3 cells via the interaction of antibody-antigen.

Figure 7A:
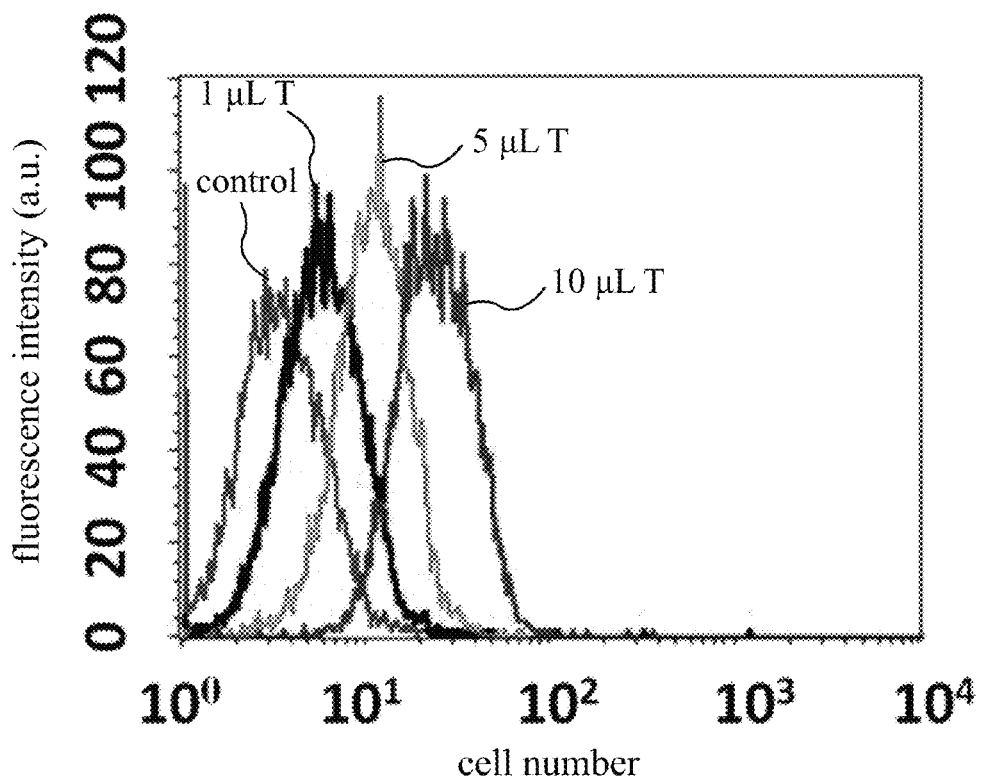
FIG. 7A shows flow cytometry analysis results of SkBr3 cells added with various amounts of trastuzumab-DENC encapsulating Dox.

FIG. 7A shows flow cytometry analysis results of SkBr3 cells added with various amounts of trastuzumab-DENC encapsulating Dox. In FIG. 7A, the trastuzumab-DENC encapsulating Dox is denoted as T, and the addition amount of the trastuzumab-DENC encapsulating Dox for the curve denoted as control was zero. It can be seen that more SkBr3 cells have more intense fluorescence when the addition amount of trastuzumab-DENC encapsulating Dox was more. This result showed that the trastuzumab-DENC encapsulating Dox can recognize the SkBr3 cells and bind onto the surface of SkBr3 cells.

Figure 7B:
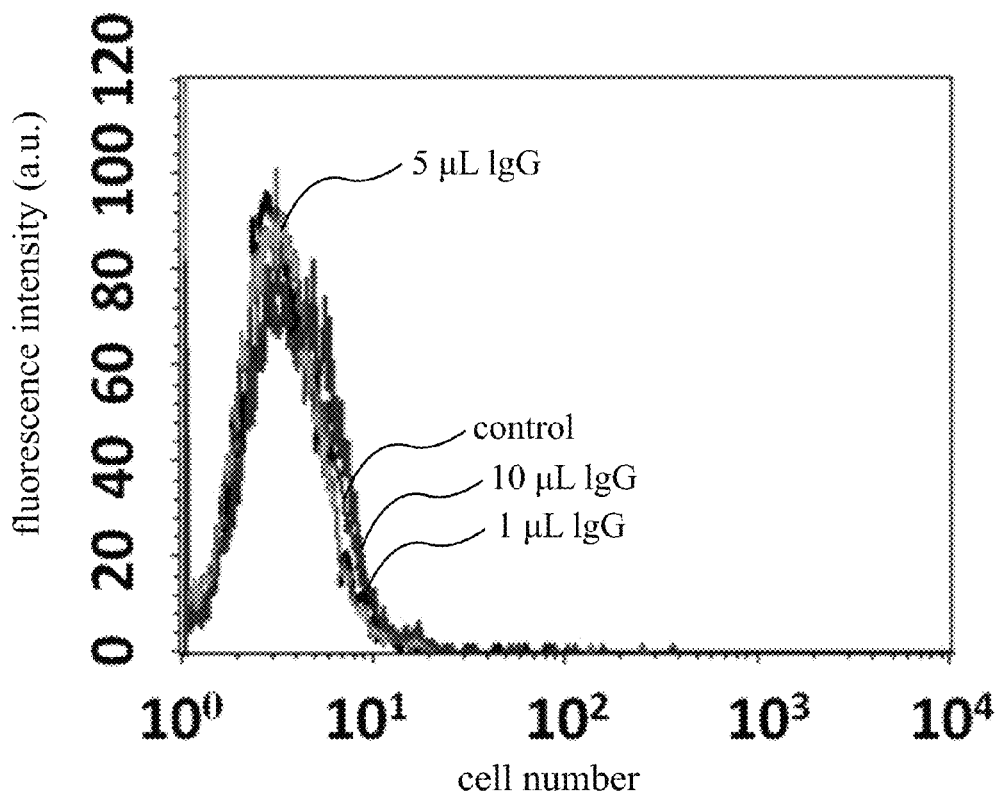
FIG. 7B shows flow cytometry analysis results of SkBr3 cells added with various amounts of IgG-DENC encapsulating Dox.

FIG. 7B shows flow cytometry analysis results of SkBr3 cells added with various amounts of IgG-DENC encapsulating Dox. In FIG. 7B, the IgG-DENC encapsulating Dox is denoted as IgG, and the addition amount of the IgG-DENC encapsulating Dox for the curve denoted as control was zero. It can be seen that no matter the addition amount of the IgG-DENC encapsulating Dox was, the fluorescence intensity distribution were almost the same. This result showed that the IgG-DENC encapsulating Dox does not show any specificity to the SkBr3 cells.

In order to further confirm the results above, after respectively incubating the trastuzumab-DENC encapsulating Dox and SkBr3 cells as well as IgG-DENC encapsulating Dox and SkBr3 cells, the nuclei of the SkBr3 cells were stained by a dye of 4',6-diamidino-2-phenylindole (DAPI). The distribution of the fluorescence Dox and nuclei was observed by confocal microscopy. In addition, pure SkBr3 cells and free Dox were also observed by the confocal microscopy. The obtained results were shown in FIG. 8.

Figure 8:
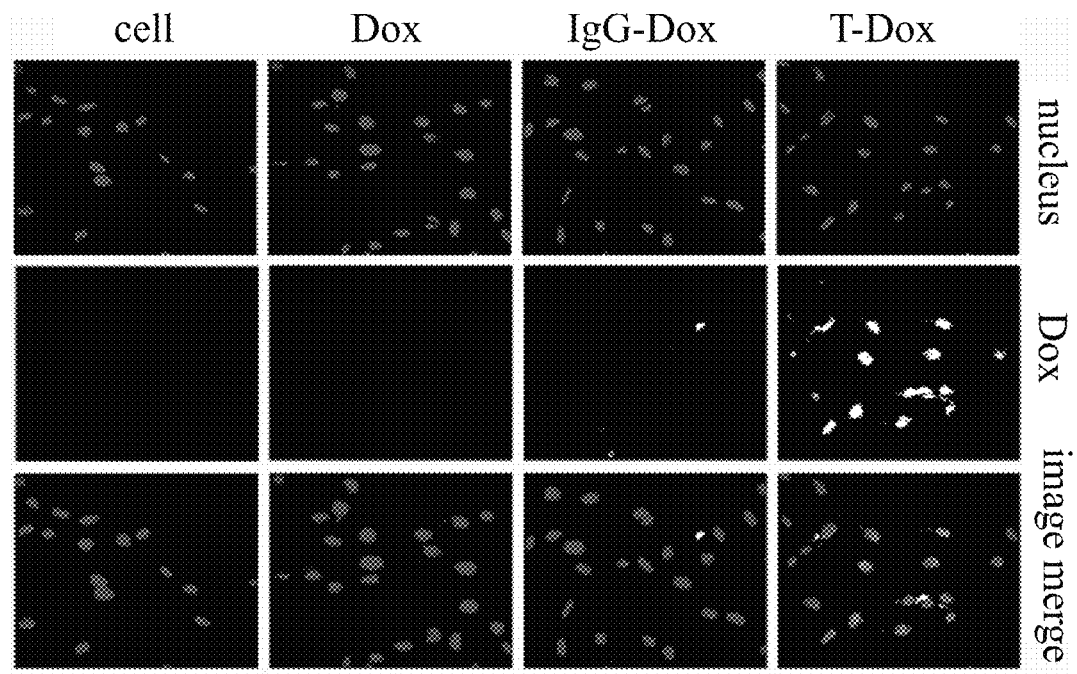
FIG. 8 shows confocal microscopic images of SkBr3 cells, unencapsulated Dox, IgG-DENC encapsulating Dox, and trastuzumab-DENC encapsulating Dox.

FIG. 8 shows confocal microscopic images of SkBr3 cells, free Dox, IgG-DENC encapsulating Dox, and trastuzumab-DENC encapsulating Dox. In FIG. 8, the columns each denoted by "cell", "Dox", "IgG-Dox", and "T-Dox" respectively represent the samples of SkBr3 cells, free Dox, IgG-DENC encapsulating Dox, and trastuzumab-DENC encapsulating Dox. The lines each denoted by "nucleus", "Dox" and "image merge" respectively represent the positions of nuclei, Dox, as well as an overlapping image of the positions of nuclei and Dox.

FIG. 8 shows that the positions of trastuzumab-DENC encapsulating Dox and the nuclei of SkBr3 cells had many overlaps. This means that trastuzumab-DENC encapsulating Dox really could recognize SkBr3 cells. However, in other samples, almost only nuclei could be observed, and almost no Dox images were observed to overlap the nuclei images. This means that other samples were almost not attached on the SkBr3 cells, i.e. other samples could not recognize SkBr3 cells.

Embodiment 9

Cytotoxicity Effect of Various DENCs on HER-2 Overexpressing Cells

In this embodiment, the cytotoxicity of various DENCs to HER-2 overexpressing cells was studied. The shell of the DENC was a mixture of PVA having a molecular weight of 16000 and TPMAA. The addition amount of TPMAA was 1 wt %, and the modification percentage of TPMAA was 37%.

The unconjugated vacant DENC (the control group), DENC encapsulating PTX (PTX group), DENC encapsulating Dox (Dox group), trastuzumab-DENC (T group), trastuzumab-DENC encapsulating PTX (T-PTX group), DENC encapsulating PTX and Dox (PTX-Dox), trastuzumab-DENC encapsulating PTX and Dox (T-PTX-Dox) were respectively added into SkBr3 cell cultures and then respectively co-cultured at 37° C. for 24 hours. Next, MTT assay was used to assess cell viability of each sample. The obtained results are listed in table 4 below and shown in FIG. 9

TABLE 4

Cytotoxicity effect of various DENCs on SkBr3 cells

| Carriers | Cell viability (%) | Cell viability percentage of trastuzumab-DENC* |
|---|---|---|
| Unconjugated vacant DENC (control) | 100.99 ± 1.01 | 74.62% |
| trastuzumab-conjugated vacant DENC (T) | 75.36 ± 3.86 | |
| DENC encapsulating PTX (PTX) | 56.40 ± 4.40 | 47.73% |
| trastuzumab-DENC encapsulating PTX (T-PTX) | 26.92 ± 3.50 | |
| DENC encapsulating Dox (Dox) | 34.80 ± 4.33 | 83.93% |
| trastuzumab-DENC encapsulating Dox (T-Dox) | 29.21 ± 3.34 | |
| DENC encapsulating PTX and Dox (PTX-Dox) | 23.60 ± 3.25 | 59.11% |
| trastuzumab-DENC encapsulating PTX and Dox (T-PTX-DOX) | 13.95 ± 2.89 | |

*calculated by (the cell viability of trastuzumab-DENC/the cell viability of DENC) × 100%

Figure 9:
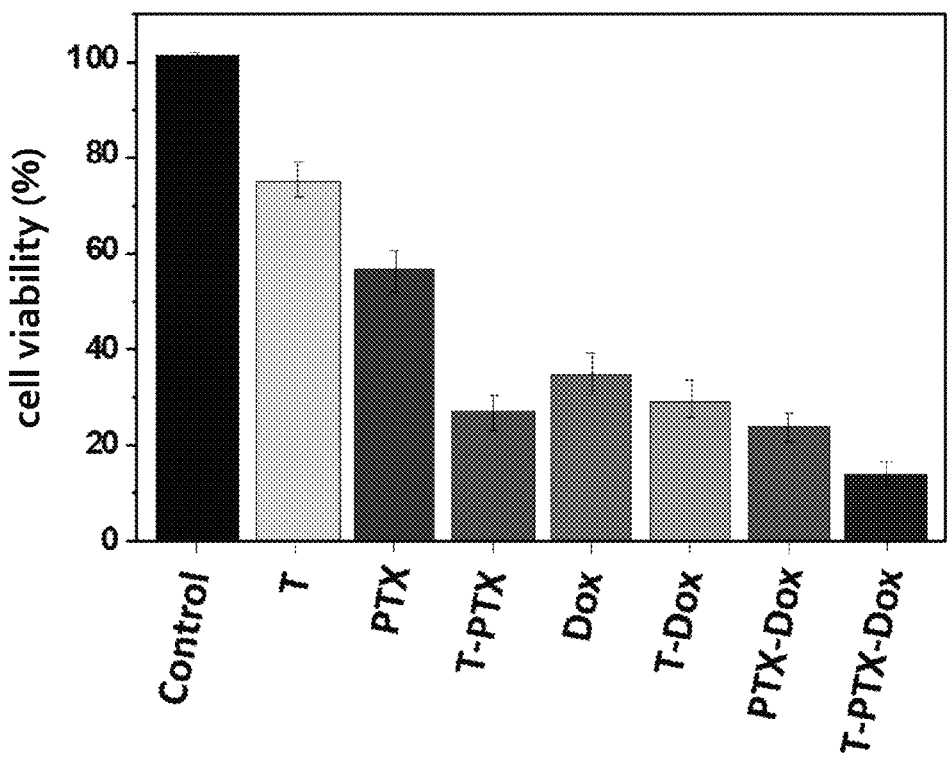
FIG. 9 shows the cell viability of the SkBr3 cells after the SkBr3 cells incubated with various samples.

From the results shown in table 4 and FIG. 9, it can be known that the vacant DENC did not have cytotoxicity effect on the SkBr3 cells and thus was nontoxic to the SkBr3 cells. However, after the vacant DENC conjugated with trastuzumab, the cell viability was decreased to about 75%. Comparing the cell viability of the DENC encapsulating PTX before and after conjugated with trastuzumab, the cell viability was decreased from about 56% to about 27%, which is only about 48% of the DENC encapsulating PTX before conjugated with trastuzumab. Comparing the cell viability of the DENC encapsulating Dox before and after conjugated with trastuzumab, the cell viability was decreased from about 35% to about 29%, which is about 84% of the DENC encapsulating Dox before conjugated with trastuzumab. Comparing the cell viability of the DENC encapsulating both PTX and Dox before and after conjugated with trastuzumab, the cell viability was decreased from about 24% to about 14%, which is about 59% of the DENC encapsulating both PTX and Dox before conjugated with trastuzumab.

From the comparisons above, it can be known that after conjugated with trastuzumab, all kinds of DENCs have a better cytotoxicity effect on the SkBr3 cells.

Embodiment 10

In Vivo Animal Experiments

In this embodiment, nude mice bearing SkBr3 solid tumors were used to perform in vivo animal experiments. The shell of the DENCs composed of a mixture of PVA having a molecular weight of 16000 and TPMAA. The addition amount of TPMAA was 1 wt %, and the modification percentage of TPMAA was 37%. The shell had been linked to a dye Cyanine 5.5 (Cy5.5).

First, the distribution of the DENCs in nude mice was observed by using a non-invasion in vivo imaging system (IVIS). A 3700 G magnet was attached to the tumor on the left side of the nude mice, and no magnets were attached to the tumor on the right side of the nude mice. The observed results of the first day and the third day after injecting the DENCs into the nude mice under IVIS were shown in FIGS. 10A and 10B.

In the image of the first day shown in FIG. 10A, a large amount of DENCs were accumulated on the both sites of the tumor 110a on the left side and the tumor 120a on the right side. However, in the image of the third day shown in FIG. 10B, the accumulative amount of the DENCs on the left tumor 110b was much greater than the accumulative amount of the DENCs on the right tumor 120b, and the accumulative amount of the left tumor 110b was about two times of the accumulative amount of the right tumor 120b. Therefore, an external applied magnetic field indeed can affect the distribution of the magnetic-sensitive DENCs in the nude mice.

Next, nude mice xenograft tumor model was used to analyze the therapeutic effect of various DENCs. In the experiment, the tested various DENCs were injected into the nail veins of nude mice respectively at the first, fifth, ninth, and thirteenth days to treat the tumor. Then, the IVIS was used to observe the tumor size during the 1-30 days. The obtained results were shown in FIG. 11.

The experimental groups shown in FIG. 11 include saline, vacant DENC, DENC encapsulating PTX (PTX), DENC encapsulating Dox (Dox), trastuzumab-DENC encapsulating PTX (T-PTX), DENC encapsulating PTX and Dox (PTX-Dox), trastuzumab-DENC encapsulating PTX and Dox but no applied magnetic field (T-PTX-DOX No MT), and trastuzumab-DENC encapsulating PTX and Dox (T-PTX-DOX). Each experiment group had a 2000 G magnet attached on the tumor site, only the group of T-PTX-DOX No MT did not has a magnet attached on the tumor site.

From the results shown in FIG. 11, it can be known that the therapy effect of the T-PTX-DOX group was the best, and the tumor size was increased to only 1.96 times of the original tumor size after 30 days. However, for the saline group, the tumor size was increased to 17.6 times of the original tumor size after 30 days.

Embodiment 11

Antibody-DENC Containing Mixture of PVA and PVA-TPMAA Copolymer

In this embodiment, DENCs containing a mixture of PVA and PVA-TPMAA copolymer were prepared by the double emulsifying method in FIG. 2B. The encapsulated drug had hydrophilic doxorubicin (Dox) and hydrophobic paclitaxel (PTX) as examples. These two drugs are common chemotherapy drugs for cancer therapy. The DENCs containing mixture of PVA and PVA-TPMAA copolymer were then conjugated with an antibody on the shells.

The preparation method of the DENCs containing mixture of PVA and PVA-TPMAA copolymer was similar to the DENCs containing a mixture of PVA and TPMAA in embodiment 6. The only difference was that the second aqueous solution of PVA and TPMAA was replaced by 2 wt % of PVA-TPMAA copolymer aqueous solution, and the modification percentage of the TPMAA in PVA-TPMAA copolymer was 37%. Finally, the obtained trastuzumab-DENCs containing mixture of PVA and PVA-TPMAA copolymer was dispersed in deionized water.

First, the content of TPMAA in PVA-TPMAA copolymer was investigated to see the effect on the antibody conjugation percentage, DENC diameter, and encapsulating efficiency. The obtained results are listed in table 5 below. From table 5, it can be known that the antibody conjugation percentage was greater when the TPMAA content was more, since the antibodies needed thiol groups of TPMAA to link with the DENCs. In addition, the higher the antibody conjugation percentage was, the larger the DENC's diameter was. The encapsulating efficiency of drugs was not affected much by the TPMAA content, and thus not by the antibody conjugation percentage. It may be that the drugs had been encapsulated in the DENCs before the antibodies were conjugated with the DENCs.

TABLE 5

Effect of TPMAA content in PVA-TPMAA copolymer on the antibody conjugation percentage, DENC's diameter, and drug's encapsulating efficiency

| Molar ratio of PVA:TPMAA in copolymer | Antibody conjugation percentage (%) | DENC's diameter (nm) | Encapsulating efficiency of PTX (%) | Encapsulating efficiency of Dox (%) |
|---|---|---|---|---|
| 6:1 | 50.92 | 156.43 | 96.20 | 82.12 |
| 5:1 | 64.29 | 167.21 | 99.10 | 80.67 |
| 4:1 | 77.47 | 175.23 | 96.61 | 81.30 |
| 3:1 | 84.26 | 198.20 | 98.45 | 78.21 |

Next, the volatile temperature and volatile time of the organic solvent chloroform in the preparation was investigated to see the effect on the DENC's diameter and drug's encapsulating efficiency. The molar ratio of PVA to TPMAA of the PVA-TPMAA copolymer was 4:1. The obtained results are listed in table 6 below. In table 6, the volatile temperature and volatile time of chloroform did not have obvious effect on the DENC's diameter and drug's encapsulating efficiency below 55° C.

TABLE 6

Effect of volatile temperature and volatile time of organic solvent chloroform on DENC's diameter and drug's encapsulating efficiency

| Volatile temperature (° C.) | Volatile time (hr) | diameter (nm) | Encapsulating efficiency of PTX (%) | Encapsulating efficiency of Dox (%) |
|---|---|---|---|---|
| 25° C. | 4 | 164.3 | 95.50 | 79.32 |
| | 5 | 162.6 | 94.64 | 77.34 |
| 35° C. | 3 | 159.7 | 97.12 | 82.43 |
| | 4 | 158.1 | 96.67 | 81.30 |
| | 5 | 159.3 | 96.10 | 80.33 |
| 45° C. | 2.5 | 159.1 | 98.20 | 81.70 |
| | 3 | 157.5 | 98.00 | 81.46 |
| | 4 | 158.6 | 96.56 | 81.23 |
| | 5 | 155.3 | 94.40 | 80.67 |
| 55° C. | 1 | 164.9 | 98.87 | 83.43 |
| | 2 | 157.2 | 98.30 | 82.23 |
| | 3 | 160.5 | 97.62 | 81.78 |
| | 4 | 154.7 | 97.20 | 81.21 |

The effect of the emulsifying time on the DENC's diameter and drug's encapsulating efficiency was subsequently investigated. The molar ratio of PVA to TPMAA in PVA-TPMAA copolymer was 4:1. The obtained result was listed in table 7 below. In table 7, the length of the first and the second emulsifying time did not have obvious effect on the DENC's diameter and drug's encapsulating efficiency.

TABLE 7

Effect of emulsifying time on DENC's diameter and drug's encapsulating efficiency

| Emulsifying time (s) | | Diameter (nm) | Encapsulating efficiency of PTX (%) | Encapsulating efficiency of Dox (%) |
|---|---|---|---|---|
| first | second | | | |
| 15 | 35 | 161.1 | 93.12 | 77.65 |
| | 45 | 158.5 | 95.14 | 78.54 |
| | 55 | 162.1 | 96.50 | 78.91 |
| 20 | 35 | 157.8 | 94.34 | 79.76 |
| | 45 | 158.1 | 96.05 | 80.45 |
| | 55 | 162.4 | 96.43 | 80.73 |

The effect of PVA molecular weight and TPMAA content of PVA-TPMAA copolymer on the product morphology was investigated. The obtained result was listed in table 8 below. In table 8, when the molecular weight of PVA was from 25000 to 61000, the diameter of the DENC was increased as the TPMAA content was increased. When PVA has a molecular weight of 47000, about half number of the nanostructures had the core-shell structure. When the PVA had a molecular weight of 61000, only a few number of the nanostructures had the core-shell structure. When the PVA had a molecular weight of 78000, no nanocapsules were formed. This result shows that no nanocapsules will be formed when the molecular weight of PVA was too large.

TABLE 8

Effect of PVA molecular weight and TPMAA content of PVA-TPMAA copolymer on the product morphology

| PVA MW | TPMAA's content (mol %) | Core-shell structure | Diameter (nm) |
|---|---|---|---|
| 25000 | 10 | Yes | 135.6 |
| | 20 | Yes | 143.4 |
| | 30 | Yes | 154.6 |

TABLE 8-continued

Effect of PVA molecular weight and TPMAA content of PVA-TPMAA copolymer on the product morphology

| PVA MW | TPMAA's content (mol %) | Core-shell structure | Diameter (nm) |
|---|---|---|---|
| 31000 | 10 | Yes | 131.6 |
|  | 20 | Yes | 136.8 |
|  | 30 | Yes | 142.3 |
| 47000 | 10 | Half | 141.5 |
|  | 20 | Half | 145.3 |
|  | 30 | Half | 149.8 |
| 61000 | 10 | Few | 124.3 |
|  | 20 | Few | 129.1 |
|  | 30 | Few | 133.2 |
| 78000 | 10 | No | 116.5 |
|  | 20 | No | 125.6 |
|  | 30 | No | 134.4 |

Embodiment 12

Antibody-Conjugated Carrier Containing PVA/TPVA Mixture

In this embodiment, double-emulsion nanocapsules (i.e. DENCs) containing a mixture of PVA and TPVA were prepared by the double emulsifying method in FIG. 2B. The exemplary drugs used were hydrophilic doxorubicin (Dox) and hydrophobic paclitaxel (PTX). These two drugs are common chemotherapy drugs for cancer therapy. The DENCs containing a mixture of PVA and TPVA were then conjugated with antibody on the shell's surface by the method of FIG. 2C.

The preparation method of the DENCs containing mixture of PVA and TPVA was similar to the DENCs containing a mixture of PVA and TPMAA in embodiment 6. The only difference was that the second aqueous solution of PVA and TPMAA was replaced by 2 wt % of TPVA aqueous solution, and the modification percentage of TPVA was 30%. Finally, the obtained trastuzumab-DENCs containing mixture of PVA and TPVA was dispersed in deionized water.

First, the TPVA content was investigated to see the effect on the antibody conjugation percentage, DENC's diameter, and encapsulating efficiency. The obtained results were listed in table 9 below. In table 9, the antibody conjugation percentage was greater when the TPVA content was more, since the antibodies needed thiol groups of TPVA to link with the DENCs. In addition, the higher the antibody conjugation percentage was, the larger the DENC's diameter was. The encapsulating efficiency of drugs was not affected much by the TPVA content, and thus not by the antibody conjugation percentage. It may be that the drugs had been encapsulated in the DENCs before the antibodies were conjugated with the DENCs.

TABLE 9

Effect of TPVA content on the antibody conjugation percentage, DENC's diameter, and drug's encapsulating efficiency

| TPVA content (mol %) | antibody conjugation percentage (%) | DENC's diameter (nm) | Encapsulating efficiency of PTX (%) | Encapsulating efficiency of Dox (%) |
|---|---|---|---|---|
| 10 | 11.85 | 135.3 | 94.11 | 79.32 |
| 20 | 23.50 | 147.5 | 92.31 | 77.31 |
| 30 | 40.65 | 165.3 | 92.81 | 78.35 |
| 35 | 54.53 | 173.4 | 95.25 | 79.89 |

The effect of the emulsifying time on the DENC's diameter and drug's encapsulating efficiency was subsequently investigated. The TVPA content was 30 mol %, and the molecular weight of PVA was 16000. The obtained result was listed in table 10 below. In table 10, the length of the first and the second emulsifying time does not obvious effect on the DENC's diameter and drug's encapsulating efficiency.

TABLE 10

Effect of emulsifying time on DENC's diameter and drug's encapsulating efficiency

| Emulsifying time (s) | | Diameter (nm) | Encapsulating efficiency of PTX (%) | Encapsulating efficiency of Dox (%) |
|---|---|---|---|---|
| first | second | | | |
| 15 | 35 | 131.4 | 92.1 | 77.2 |
|  | 45 | 137.6 | 95.1 | 79.2 |
|  | 55 | 134.1 | 92.6 | 78.4 |
| 20 | 35 | 133.4 | 90.5 | 80.3 |
|  | 45 | 131.1 | 92.7 | 75.9 |
|  | 55 | 136.6 | 93.1 | 78.3 |

The effect of PVA molecular weight and TPVA content on the product morphology was investigated. The obtained results were listed in table 11 below. In table 11, when the molecular weight of PVA was from 25000 to 61000, the diameter of the DENC was increased as the TPVA content was increased. When PVA has a molecular weight of 47000, about half number of the nanostructures had the core-shell structure. When the PVA had a molecular weight of 61000, only a few number of the nanostructures had the core-shell structure. When the PVA had a molecular weight of 78000, no nanocapsules were formed. This result shows that no nanocapsules will be formed when the molecular weight of PVA was too large.

TABLE 11

Effect of PVA molecular weight and TPVA content of PVA-TPMAA copolymer on the product morphology

| PVA MW | TPVA content (mol %) | Core-shell structure | Carrier's diameter (nm) |
|---|---|---|---|
| 25000 | 10 | Yes | 126.4 |
|  | 20 | Yes | 131.5 |
|  | 30 | Yes | 137.6 |
| 31000 | 10 | Yes | 121.6 |
|  | 20 | Yes | 135.8 |
|  | 30 | Yes | 138.3 |
| 47000 | 10 | Half | 137.5 |
|  | 20 | Half | 146.3 |
|  | 30 | Half | 151.8 |
| 61000 | 10 | Few | 108.4(solid core)/ 141.6(core-shell) |
|  | 20 | Few | 112.5(solid core)/ 148.1(core-shell) |
|  | 30 | Few | 119.4(solid core)/ 153.4(core-shell) |
| 78000 | 10 | No | 116.5 |
|  | 20 | No | 125.6 |
|  | 30 | No | 134.4 |

Embodiment 13

Antibody-DENCs Containing PVA/PAA Mixture

In this embodiment, double-emulsion nanocapsules (i.e. DENCs) containing a mixture of PVA and PAA were prepared by the double emulsifying method in FIG. 2B. The exemplary drugs used were hydrophilic doxorubicin (Dox) and hydrophobic paclitaxel (PTX). These two drugs are common chemotherapy drugs for cancer therapy. The DENCs containing a mixture of PVA and PAA were then conjugated with antibody on the shell's surface by the method of FIG. 2C.

The preparation method of the DENCs containing mixture of PVA and PAA was similar to the DENCs containing a mixture of PVA and TPMAA in embodiment 6. The first difference was that the second aqueous solution of PVA and TPMAA was replaced by an aqueous solution of PVA and PAA. In the aqueous solution of PVA and PAA, the concentration of PVA was 20 mg/mL, and the concentration of PAA was 2 mg/mL. The second difference was that the coupling agent of SMCC was replaced by a combination of EDC and sulfo-NHS to link the primary amine group of the breast cancer antibody trastuzumab to the carboxylic group of PAA. The molecular weight of the PVA was 16000.

In the reaction of the breast cancer antibody trastuzumab and the coupling agent, 0.1 M of MES buffer solution containing 0.1 M of MES and 0.5 M of NaCl and having a pH value of 6.0 was first prepared. Then, DENCs, 50 µg of EDC, and 60 µg of Sulfo-NHS were sequentially added into the 3 mL of MES buffer solution. The mixture was stirred and reacted for 15 minutes. 1 µL of 2-mercaptoethanol was then added into the above MES buffer solution to stop the activation reaction of EDC. Next, high concentration of PBS solution was added into the MES buffer solution to increase the pH value to more than 7. Subsequently, 500 µg of breast cancer antibody trastuzumab was added and reacted at room temperature for 2 hours to obtain trastuzumab-DENCs.

The obtained trastuzumab-DENCs were dispersed in deionized water, and unreacted agents were removed after the dispersion solution was centrifuged at 7000 rpm. The steps of dispersion and centrifugation were repeated for several times to purify the trastuzumab-DENCs. The purified trastuzumab-DENCs were dispersed in a solvent, such as saline.

Figure 12:
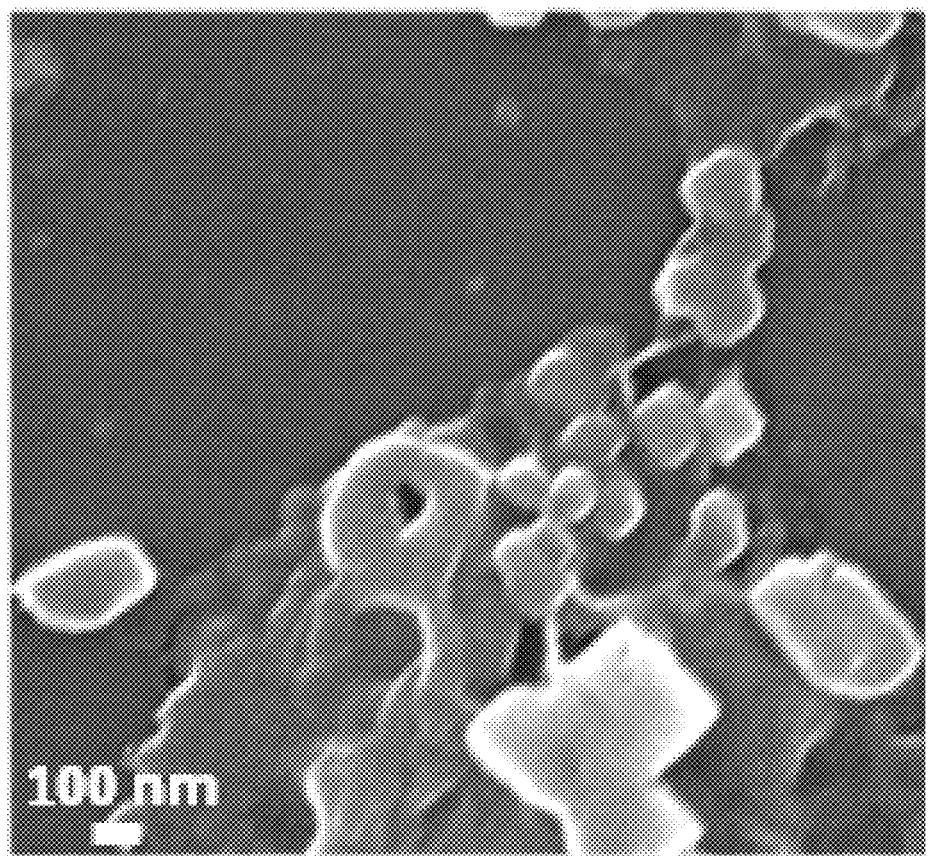
FIG. 12 was a SEM image of trastuzumab-DENCs containing a mixture of PVA and PAA.

FIG. 12 was a SEM image of trastuzumab-DENCs containing a mixture of PVA and PAA. In FIG. 12, it can be observed that the spherical shape of the unconjugated DENC was changed to the irregular shape of trastuzumab-DENCs. This may be caused by conjugating the DENCs with the breast cancer antibody trastuzumab. However, it still can be seen that the trastuzumab-DENCs had a hollow structure from the black and white contrast of the SEM image. In addition, the obtained trastuzumab-DENCs containing PVA/PAA mixture can be uniformly dispersed in solution without forming precipitation. Therefore, the trastuzumab-DENCs containing PVA/PAA mixture were similar to the trastuzumab-DENCs containing PVA/TPMAA mixture in Embodiment 6.

Embodiment 14

Antibody-DENCs Containing PVA/PMAA Mixture

In this embodiment, double-emulsion nanocapsules (i.e. DENCs) containing a mixture of PVA and PMAA were prepared by the double emulsifying method in FIG. 2B. The exemplary drugs used were hydrophilic doxorubicin (Dox) and hydrophobic paclitaxel (PTX). These two drugs are common chemotherapy drugs for cancer therapy. The DENCs containing a mixture of PVA and PMAA were then conjugated with antibody on the shell's surface by the method of FIG. 2C.

The preparation method of the DENCs containing mixture of PVA and PMAA was similar to the DENCs containing a mixture of PVA and TPMAA in embodiment 6. The only difference was that the second aqueous solution of PVA and TPMAA was replaced by an aqueous solution containing a mixture of PVA and PMAA, and the molecular weight of the PVA was 16000.

The obtained trastuzumab-DENCs containing mixture of PVA and PMAA also had an irregular morphology observed under SEM, but still maintain a hollow structure. In addition, the trastuzumab-DENCs containing mixture of PVA and PMAA also could be uniformly dispersed in solution without forming precipitation. Therefore, the trastuzumab-DENCs containing PVA/PMAA mixture were similar to the trastuzumab-DENCs containing PVA/TPMAA mixture in Embodiment 6.

Embodiment 15

Antibody-DENCs Containing PVA/CMPVA Mixture

In this embodiment, double-emulsion nanocapsules (i.e. DENCs) containing a mixture of PVA and CMPVA were prepared by the double emulsifying method in FIG. 2B. The exemplary drugs used were hydrophilic doxorubicin (Dox) and hydrophobic paclitaxel (PTX). These two drugs are common chemotherapy drugs for cancer therapy. The DENCs containing a mixture of PVA and CMPVA were then conjugated with antibody on the shell's surface by the method of FIG. 2C The preparation method of the DENCs containing mixture of PVA and CMPVA was similar to the DENCs containing a mixture of PVA and PAA in embodiment 13. The only difference was that the second aqueous solution of PVA and PAA was replaced by an aqueous solution containing a mixture of PVA and CMPVA. The molecular weight of the PVA was 16000, and the modification percentage of the CMPVA was 30%.

First, the CMPVA content was investigated to see the effect on the antibody conjugation percentage, DENC's diameter, and encapsulating efficiency. The obtained results were listed in table 12 below. In table 12, the antibody conjugation percentage was greater when the CMPVA content was more, since the antibodies needed carboxylic groups of CMPVA to link with the DENCs. In addition, the higher the antibody conjugation percentage was, the larger the DENC's diameter was.

The encapsulating efficiency of drugs was not affected much by the CMPVA content, and thus not by the antibody conjugation percentage. It may be that the drugs had been encapsulated in the DENCs before the antibodies were conjugated with the DENCs. However, comparing the DENCs containing the mixture of PVA and CMPVA (table 12) and the DENCs containing the mixture of PVA and TPVA (table 9), since protons are easily dissociated from the carboxylic groups of CMPVA, the encapsulating efficiency of Dox by DENCs containing the mixture of PVA and CMPVA was increased by 5-10%.

TABLE 12

Effect of CMPVA content on the antibody conjugation percentage, DENC's diameter, and drug's encapsulating efficiency

| CMPVA content (mol %) | antibody conjugation percentage (%) | DENC's diameter (nm) | Encapsulating efficiency of PTX (%) | Encapsulating efficiency of Dox (%) |
|---|---|---|---|---|
| 10 | 17.82 | 143.6 | 96.31 | 84.34 |
| 20 | 29.10 | 149.1 | 97.10 | 83.65 |
| 30 | 43.25 | 166.5 | 95.71 | 87.65 |
| 40 | 61.32 | 169.6 | 96.75 | 88.53 |
| 50 | 85.64 | 178.7 | 95.67 | 89.46 |

Next, the effect of the emulsifying time on the DENC's diameter and drug's encapsulating efficiency was subsequently investigated. The CMPVA content was 30 mol %, and the molecular weight of PVA was 16000. The obtained results were listed in table 13 below. In table 13, the length of the first and the second emulsifying time did not have obvious effect on the DENC's diameter and drug's encapsulating efficiency.

TABLE 13

Effect of emulsifying time on DENC's diameter and drug's encapsulating efficiency

| Emulsifying time (s) first | Emulsifying time (s) second | Diameter (nm) | Encapsulating efficiency of PTX (%) | Encapsulating efficiency of Dox (%) |
|---|---|---|---|---|
| 15 | 35 | 153.4 | 95.21 | 79.32 |
|    | 45 | 148.2 | 96.70 | 77.31 |
|    | 55 | 156.2 | 96.10 | 78.35 |
| 20 | 35 | 154.3 | 97.25 | 79.89 |
|    | 45 | 156.3 | 94.67 | 79.32 |
|    | 55 | 149.4 | 95.31 | 77.31 |

Next, the effect of PVA molecular weight and CMPVA content on the product morphology was investigated. The obtained result was listed in table 14 below. In table 14, when the molecular weight of PVA was from 25000 to 61000, the diameter of the DENCs was increased as the CMPVA content was increased. When the PVA had a molecular weight of 61000, only a few number of the nanostructures had the core-shell structure. When the PVA had a molecular weight of 78000, no nanocapsules were formed. This result shows that no nanocapsules will be formed when the molecular weight of PVA was too large.

TABLE 14

Effect of PVA molecular weight and CMPVA content of PVA-TPMAA copolymer on the product morphology

| PVA MW | TPVA content (mol %) | Core-shell structure | Carrier's diameter (nm) |
|---|---|---|---|
| 25000 | 10 | Yes | 124.6 |
|       | 30 | Yes | 131.4 |
|       | 50 | Yes | 133.6 |
| 31000 | 10 | Yes | 121.5 |
|       | 30 | Yes | 127.6 |
|       | 50 | Yes | 131.5 |
| 47000 | 10 | Yes | 134.5 |
|       | 30 | Yes | 139.5 |
|       | 50 | Yes | 142.4 |
| 61000 | 10 | Few | 116.5 |
|       | 30 | Few | 127.1 |
|       | 50 | Few | 133.2 |
| 78000 | 10 | No  | 91.5  |
|       | 30 | No  | 96.7  |
|       | 50 | No  | 109.3 |

Embodiment 16

Antibody-Conjugated Carrier Containing Mixture of PVA-TPMAA Copolymer

In this embodiment, double-emulsion nanocapsules (i.e. DENCs) containing PVA-TPMAA copolymer were prepared by the single emulsifying method in FIG. 2A. The exemplary drugs used were hydrophilic doxorubicin (Dox) and hydrophobic paclitaxel (PTX). These two drugs are common chemotherapy drugs for cancer therapy. The DENCs containing PVA-TPMAA copolymer were then conjugated with antibody on the shell's surface by the method of FIG. 2C.

An aqueous solution of PVA-TPMAA copolymer and Dox, as well as a chloroform solution of IO-OA nanoparticles and PTX were respectively prepared. In the aqueous solution of PVA-TPMAA copolymer and Dox, the concentration of PVA-TPMAA copolymer was 20 mg/mL, and the concentration of Dox was 8 mg/mL. In the chloroform solution of IO-OA nanoparticles and PTX, the concentration of IO-OA nanoparticles was 20 mg/mL, and the concentration of Dox was 30 mg/mL.

2.5 mL of the first aqueous solution containing PVA-TPMAA copolymer and Dox, as well as 1 mL of the $CHCl_3$ solution containing IO-OA nanoparticles and PTX were mixed and emulsified by ultrasound sonication at a frequency of 20 kHz to obtain DENCs containing PVA-TPMAA copolymer. The modification percentage of the TPMAA copolymerized with PVA was 37%. The volatile $CHCl_3$ of the emulsion solution was then removed by placing the final obtained emulsion solution at an open space to evaporate the $CHCl_3$. The temperature of evaporating the $CHCl_3$ may change the morphology of the DENCs. Next, the DENCs containing PVA-TPMAA copolymer were dispersed in 3 mL of PBS solution containing 0.1 M of sodium phosphate and 0.15 M of NaCl.

Next, the breast cancer antibody trastuzumab was conjugated with the obtained DENCs containing PVA-TPMAA copolymer. The details of the conjugation method was the same as the conjugation method of Embodiment 6, and hence omitted here.

First, the TPMAA content in the PVA-TPMAA copolymer was investigated to see the effect on the antibody conjugation percentage, DENC's diameter, and encapsulating efficiency. The obtained results were listed in table 15 below. In table 15, the antibody conjugation percentage was greater when the TPMAA content was more, since the antibodies needed thiol groups of TPMAA to link with the DENCs. In addition, the higher the antibody conjugation percentage was, the larger the DENC's diameter was. The encapsulating efficiency of Dox and PTX was not affected much by the TPMAA content, and thus not by the antibody conjugation percentage. It may be that the drugs had been encapsulated in the DENCs before the antibodies were conjugated with the DENCs.

TABLE 15

Effect of TPMAA content on the antibody conjugation percentage, DENC's diameter, and drug's encapsulating efficiency

| Molar ratio of PVA to TPMAA | antibody conjugation percentage (%) | DENC's diameter (nm) | Encapsulating efficiency of PTX (%) | Encapsulating efficiency of Dox (%) |
| --- | --- | --- | --- | --- |
| 6:1 | 22.41 | 142.3 | 97.0 | 84.7 |
| 5:1 | 39.30 | 151.6 | 98.2 | 83.5 |
| 4:1 | 61.23 | 166.2 | 97.3 | 84.3 |
| 3:1 | 87.12 | 178.3 | 98.5 | 87.6 |

Embodiment 17

Antibody-Conjugated Carrier Containing TPVA

In this embodiment, double-emulsion nanocapsules (i.e. DENCs) containing TPVA were prepared by the single emulsifying method in FIG. 2A. The exemplary drugs used were hydrophilic doxorubicin (Dox) and hydrophobic paclitaxel (PTX). These two drugs are common chemotherapy drugs for cancer therapy. The DENCs containing TPVA were then conjugated with antibody on the shell's surface by the method of FIG. 2C.

The preparation method of the DENCs containing TPVA was similar to the DENCs containing PVA-TPMAA copolymer in embodiment 16. The only difference was that the aqueous solution of PVA-TPMAA copolymer and Dox was replaced by an aqueous solution containing TPVA and Dox. In the aqueous solution of TPVA and Dox, the concentration of TPVA was 20 mg/mL, and the concentration of Dox was 8 mg/mL. The used PVA had a molecular weight of 16000.

Figure 13A:
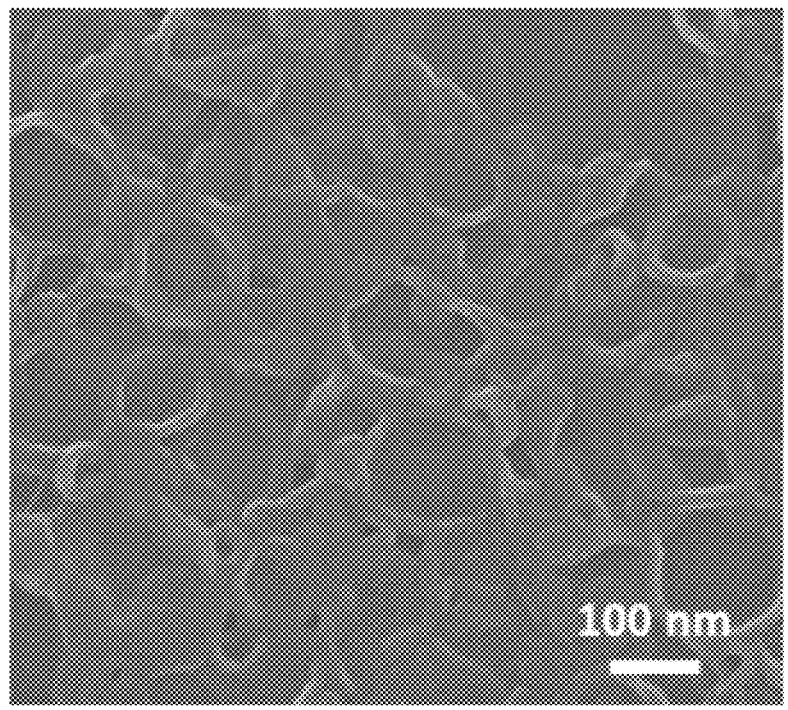
FIGS. 13A-13C are SEM images of double-emulsion nanocapsules containing TPVA having a molecular weight of 25000, 47000, and 78000, respectively.
Figure 13B:
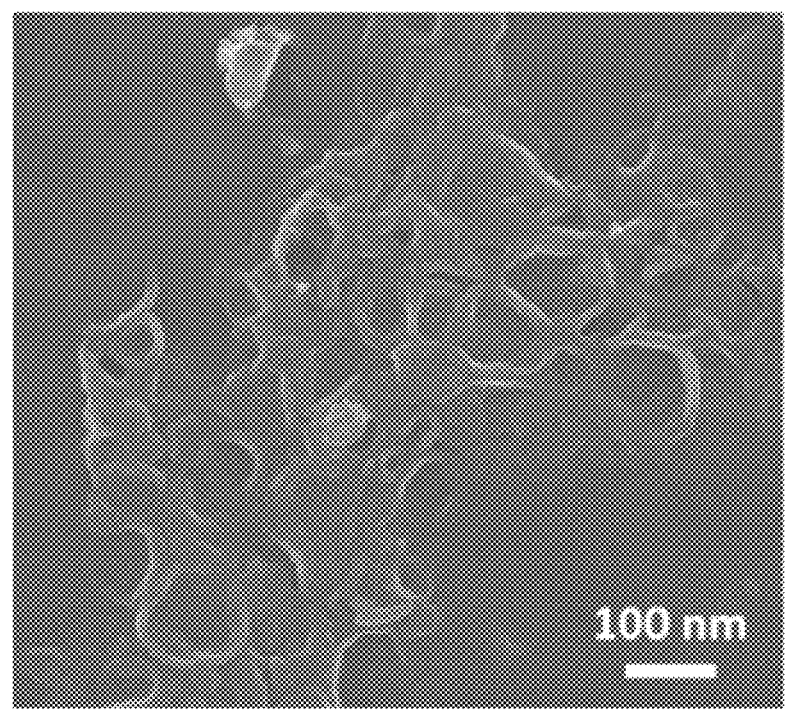
Figure 13C:
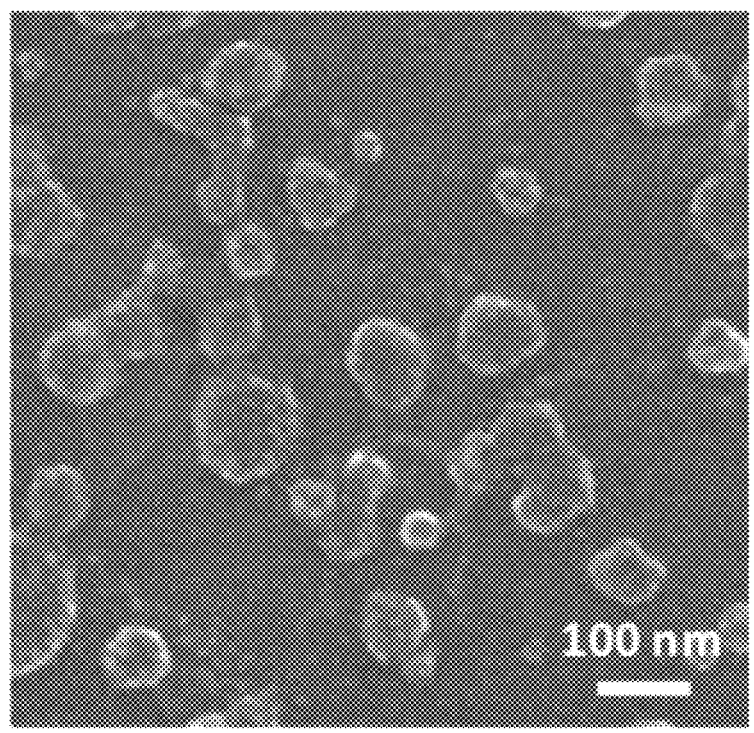

FIGS. 13A-13C are SEM images of double-emulsion nanocapsules containing TPVA having a molecular weight of 25000, 47000, and 78000, respectively. FIGS. 13A-13C show that the aggregation of the DENCs was increased as the molecular weight of TPVA was increased. The reason may be that the hydrophobicity of the DENCs was increased as the molecular weight of TPVA was increased. Especially, when the molecular weight of TPVA was 78000, which was too great to form nanostructures with core-shell structure.

First, since TPVA was obtained by modifying PVA with thioglycolic acid, the modification percentage of TPVA was investigated to see the effect on the antibody conjugation percentage, DENC's diameter, and encapsulating efficiency. The TPVA was obtained from PVA with a molecular weight of 16000, and the obtained results were listed in table 16 below. In table 16, the antibody conjugation percentage was greater when the modification percentage of TPVA was more, since the antibodies needed thiol groups of TPVA to link with the DENCs. In addition, the higher the antibody conjugation percentage was, the larger the DENC's diameter was. The encapsulating efficiency of drugs was not affected much by the modification percentage of PVA, and thus not by the antibody conjugation percentage. It may be that the drugs had been encapsulated in the DENCs before the antibodies were conjugated with the DENCs.

TABLE 16

Effect of TPVA modification percentage on the antibody conjugation percentage, DENC's diameter, and drug's encapsulating efficiency

| Modification percentage of TPVA (mol %) | antibody conjugation percentage (%) | DENC's diameter (nm) | Encapsulating efficiency of PTX (%) | Encapsulating efficiency of Dox (%) |
| --- | --- | --- | --- | --- |
| 10 | 8.54 | 121.3 | 95.65 | 74.58 |
| 20 | 13.55 | 133.4 | 98.25 | 76.80 |
| 30 | 29.97 | 141.6 | 94.60 | 78.80 |
| 35 | 50.88 | 155.3 | 98.50 | 77.41 |

Embodiment 18

Antibody-Conjugated Carrier Containing CMPVA

In this embodiment, double-emulsion nanocapsules (i.e. DENCs) containing CMPVA were prepared by the single emulsifying method in FIG. 2A. The exemplary drugs used were hydrophilic doxorubicin (Dox) and hydrophobic paclitaxel (PTX). These two drugs are common chemotherapy drugs for cancer therapy. The DENCs containing CMPVA were then conjugated with antibody on the shell's surface by the method of FIG. 2C.

The preparation method of the DENCs containing CMPVA was similar to the DENCs containing PVA-TPMAA copolymer in embodiment 16. The only difference was that the aqueous solution of PVA-TPMAA copolymer and Dox was replaced by an aqueous solution containing CMPVA and Dox. In the aqueous solution of CMPVA and Dox, the concentration of CMPVA was 20 mg/mL, and the concentration of Dox was 8 mg/mL. The used PVA had a molecular weight of 16000.

The method of conjugating antibody was similar to the DENCs containing mixture of PVA and PAA in embodiment 13. The coupling agent was a combination of EDC and sulfo-NHS to linking the carboxylic group of CMOVA with the primary amine group of the breast cancer antibody trastuzumab.

Since CMPVA was obtained by modifying PVA, the modification percentage of CMPVA was investigated to see the effect on the antibody conjugation percentage, DENC's diameter, and encapsulating efficiency. The obtained CMPVA was obtained from PVA with a molecular weight of 16000, and the obtained results were listed in table 17 below. In table 17, the antibody conjugation percentage was greater when the modification percentage of PVA was more, since the antibodies need thiol groups of PVA to link with the DENCs. In addition, the higher the antibody conjugation percentage was, the larger the DENC's diameter was.

The encapsulating efficiency of drugs was not affected much by the modification percentage of PVA, and thus not by the antibody conjugation percentage. It may be that the drugs had been encapsulated in the DENCs before the antibodies were conjugated with the DENCs. However, comparing the DENCs containing the CMPVA (table 17) and the DENCs containing the mixture of PVA and CMPVA (table 12), since only CMPVA was used in the single emulsifying method, the carboxylic groups could distribute on the inner surface and the outer surface of the DENCs' shells. In addition, since protons are easily dissociated from the carboxylic groups of CMPVA, the encapsulating efficiency of Dox by DENCs containing the mixture of PVA and CMPVA was increased by 1-5%

TABLE 17

Effect of PVA modification percentage on the antibody conjugation percentage, DENC's diameter, and drug's encapsulating efficiency

| Modification percentage of CMPVA (mol %) | antibody conjugation percentage (%) | DENC's diameter (nm) | Encapsulating efficiency of PTX (%) | Encapsulating efficiency of Dox (%) |
|---|---|---|---|---|
| 10 | 14.50 | 133.5 | 94.58 | 87.41 |
| 20 | 26.12 | 141.2 | 96.40 | 86.73 |
| 30 | 38.40 | 149.5 | 93.25 | 89.43 |
| 40 | 55.68 | 156.3 | 94.87 | 91.44 |
| 50 | 71.58 | 164.8 | 96.55 | 93.20 |

In light of the foregoing, the single emulsifying method may be used to let the linking PVA form double-emulsion nanocapsules to present linking groups on both the inner surface and the outer surface of the double-emulsion nanocapsules. The double emulsifying method may also be used to let a mixture of PVA and a linking polymer form double-emulsion nanocapsules to present linking groups on outer surface of the double-emulsion nanocapsules. The linking groups can be used to bind the needed antibody, and thus the antibody can be bound on the outer surface of the double-emulsion nanocapsules. Therefore, the double-emulsion nanocapsules encapsulating drugs can target to some certain cells to conduct targeted therapy. Moreover, an external applied magnetic field can be further used to increase the accumulative amount of drugs, and the therapy effect can be further increased.

All the features disclosed in this specification (including any accompanying claims, abstract, and drawings) may be replaced by alternative features serving the same, equivalent or similar purpose, unless expressly stated otherwise. Thus, each feature disclosed is one example only of a generic series of equivalent or similar features.

What is claimed is:

1. An antibody-conjugated double-emulsion nanocapsule, comprising:
   an aqueous core;
   an oily shell enclosing the aqueous core, wherein a composition of the oily shell comprises a polymer and a plurality of hydrophobic magnetic nanoparticles but does not comprise other polymers and surfactants, and wherein the polymer is a linking polyvinyl alcohol or a combination of polyvinyl alcohol (PVA) and a linking polymer, and the linking polyvinyl alcohol and the linking polymer have a linking group; and
   at least an antibody chemically bonded to the linking group via a coupling agent,
   wherein a diameter of the antibody-conjugated double-emulsion nanocapsule is about 50 nm to about 400 nm;
   wherein the linking polyvinyl alcohol is carboxymethylated polyvinyl alcohol (CMPVA), thiolated polyvinyl alcohol (TPVA), or a copolymer of PVA-TPMAA.

2. The antibody-conjugated double-emulsion nanocapsule of claim 1, wherein the linking group is a carboxylic group, a thiol group, an aldehyde group, an amine group, or a hydroxyl group.

3. The antibody-conjugated double-emulsion nanocapsule of claim 1, wherein the linking polymer is polyacrylic acid (PAA), polymethacrylic acid (PMAA), or thiolated polymethacrylic acid (TPMAA).

4. The antibody-conjugated double-emulsion nanocapsule of claim 1, wherein the hydrophobic magnetic nanoparticles are nanoparticles having a hydrophobic functional groups-modified surface and made from Fe2O3, Fe3O4, CoFe2O4, or MnFe2O4.

5. The antibody-conjugated double-emulsion nanocapsule of claim 1, wherein the antibody comprises breast cancer antibody of trastuzumab, colorectal cancer antibody of cetuximab, epidermal growth factor receptor antibody of panitumumab, or angiogenesis inhibitor antibody of bevacizumab.

6. The antibody-conjugated double-emulsion nanocapsule of claim 1, wherein the coupling agent is 4-(N-maleimidomethyl) cyclohexane carboxylic acid N-hydroxysuccinimide ester (SMCC), N-(3-dimethylaminopropyl)-N-ethyl carbodiimide hydrochloride (EDC), N-hydroxysulfosuccinimide sodium salt (Sulfo-NHS), or 3-(2-pyridyldithio)propionic acid N-hydroxysuccinimide ester (SPDP).

7. The antibody-conjugated double-emulsion nanocapsule of claim 1, wherein the oily shell further comprises a hydrophobic drug.

8. The antibody-conjugated double-emulsion nanocapsule of claim 1, wherein the aqueous core further comprises a hydrophilic drug.

9. A single emulsifying method of preparing an antibody-conjugated double-emulsion nanocapsule, comprising:
   preparing an aqueous solution comprising a linking polyvinyl alcohol having a linking group but not comprising other polymers and surfactants;
   preparing an organic solution comprising a plurality of hydrophobic magnetic nanoparticles;
   mixing the aqueous solution and the organic solution to form an emulsion solution comprising a plurality of double-emulsion nanocapsules;
   removing an organic solvent used by the organic solution to obtain the double-emulsion nanocapsules;
   preparing a first dispersion solution comprising the double-emulsion nanocapsules;
   preparing a second dispersion solution comprising an antibody conjugated with a coupling agent; and
   mixing the first dispersion solution and the second dispersion solution to chemically react the linking group and the coupling agent to obtain a plurality of antibody-conjugated double-emulsion nanocapsules.

10. The single emulsifying method of claim 9, wherein the linking group is a carboxylic group, a thiol group, an aldehyde group, an amine group, or a hydroxyl group.

11. The single emulsifying method of claim 9, wherein the linking polyvinyl alcohol is carboxymethylated polyvinyl alcohol (CMPVA), thiolated polyvinyl alcohol (TPVA), or a copolymer of PVA-TPMAA.

12. The single emulsifying method of claim 9, wherein the hydrophobic magnetic nanoparticles are nanoparticles having hydrophobic functional groups-modified surface and made from $Fe_2O_3$, $Fe_3O_4$, $CoFe_2O_4$, or $MnFe_2O_4$.

13. The single emulsifying method of claim 9, wherein the antibody comprises breast cancer antibody trastuzumab, colorectal cancer antibody cetuximab, epidermal growth factor receptor antibody panitumumab, or angiogenesis inhibitor antibody bevacizumab.

14. The single emulsifying method of claim 9, wherein the coupling agent is 4-(N-maleimidomethyl) cyclohexane carboxylic acid N-hydroxysuccinimide ester (SMCC), N-(3-dimethylaminopropyl)-N-ethyl carbodiimide hydrochloride (EDC), N-hydroxysulfosuccinimide sodium salt (Sulfo-NHS), or 3-(2-pyridyldithio)propionic acid N-hydroxysuccinimide ester (SPDP).

15. The single emulsifying method of claim 9, wherein the aqueous solution comprises a hydrophilic drug.

16. The single emulsifying method of claim 9, wherein the organic solution comprises a hydrophobic drug.

17. A double emulsifying method of preparing an antibody-conjugated double-emulsion nanocapsule, comprising:
preparing a first aqueous solution comprising polyvinyl alcohol but not comprising other polymers and surfactants;
preparing an organic solution comprising a plurality of hydrophobic magnetic nanoparticles;
mixing the first aqueous solution and the organic solution to form a first emulsion solution, wherein the first emulsion solution is a water-in-oil emulsion solution;
preparing a second aqueous solution comprising a combination of a linking polymer having a linking group and polyvinyl alcohol, but not comprising other polymers or other surfactants;
mixing the first emulsion solution and the second aqueous solution to form a second solution comprising a plurality of double-emulsion nanocapsules;
removing an organic solvent used by the organic solution to obtain the double-emulsion nanocapsules;
preparing a first dispersion solution comprising the double-emulsion nanocapsules;
preparing a second dispersion solution comprising an antibody conjugated with a coupling agent; and
mixing the first dispersion solution and the second dispersion solution to chemically react the linking group and the coupling agent to obtain a plurality of antibody-conjugated double-emulsion nanocapsules.

18. The double emulsifying method of claim 17, wherein the linking group is a carboxylic group, a thiol group, an aldehyde group, an amine group, or a hydroxyl group.

19. The double emulsifying method of claim 17, wherein the linking polymer is polyacrylic acid (PAA), polymethacrylic acid (PMAA), or thiolated polymethacrylic acid (TPMAA).

20. The double emulsifying method of claim 17, wherein the hydrophobic magnetic nanoparticles are nanoparticles having hydrophobic functional groups-modified surface and made from $Fe_2O_3$, $Fe_3O_4$, $CoFe_2O_4$, or $MnFe_2O_4$.

21. The double emulsifying method of claim 17, wherein the antibody comprises breast cancer antibody of trastuzumab, colorectal cancer antibody of cetuximab, epidermal growth factor receptor antibody of panitumumab, or angiogenesis inhibitor antibody of bevacizumab.

22. The double emulsifying method of claim 17, wherein the coupling agent is 4-(N-maleimidomethyl) cyclohexane carboxylic acid N-hydroxysuccinimide ester (SMCC), N-(3-dimethylaminopropyl)-N-ethyl carbodiimide hydrochloride (EDC), N-hydroxysulfosuccinimide sodium salt (Sulfo-NHS), or 3-(2-pyridyldithio)propionic acid N-hydroxysuccinimide ester (SPDP).

23. The double emulsifying method of claim 17, wherein the first aqueous solution comprises a hydrophilic drug.

24. The double emulsifying method of claim 17, wherein the organic solution comprises a hydrophobic drug.

* * * * *